United States Patent [19]
Allison et al.

[11] Patent Number: 5,855,887
[45] Date of Patent: Jan. 5, 1999

[54] BLOCKADE OF LYMPHOCYTE DOWN-REGULATION ASSOCIATED WITH CTLA-4 SIGNALING

[75] Inventors: James Patrick Allison, Berkeley; Dana R. Leach, Albany; Matthew F. Krummel, Berkeley, all of Calif.

[73] Assignee: The Regents of the University of California, Oakland, Calif.

[21] Appl. No.: 566,853

[22] Filed: Dec. 4, 1995

Related U.S. Application Data

[63] Continuation-in-part of Ser. No. 506,666, Jul. 25, 1995, abandoned.

[51] Int. Cl.⁶ .......................... A61K 39/395; G01N 33/53
[52] U.S. Cl. ...................... 424/144.1; 424/133.1; 424/139.1; 424/143.1; 435/7.24
[58] Field of Search .............. 424/130.1, 133.1, 424/135.1, 139.1, 143.1, 144.1, 810; 530/387.1, 388.22, 388.7; 514/885; 435/7.24

[56] References Cited

U.S. PATENT DOCUMENTS

| | | | |
|---|---|---|---|
| 5,434,131 | 7/1995 | Linsley | 514/2 |
| 5,556,763 | 9/1996 | Ochoa et al. | 435/7.23 |

FOREIGN PATENT DOCUMENTS

| | | |
|---|---|---|
| 0 613 944 | 9/1994 | European Pat. Off. |
| 0 682 039 | 11/1995 | European Pat. Off. |
| 93/00431 | 1/1993 | WIPO |
| 95/01994 | 1/1995 | WIPO |
| 95/03408 | 2/1995 | WIPO |
| 95/05464 | 2/1995 | WIPO |
| 95/23859 | 9/1995 | WIPO |
| 95/24217 | 9/1995 | WIPO |
| 95/33770 | 12/1995 | WIPO |
| 95/34320 | 12/1995 | WIPO |
| 96/14865 | 5/1996 | WIPO |

OTHER PUBLICATIONS

Walnus, TL. *Immunity* 1:405–413, Aug. 1994.
Kearney ER J.Immunol 155:1032–1036, Aug. 1995.
Wu et al., "CTLA–4–B7 Interaction is Sufficient to Costimulate T Cell Clonal Expansion," *J. Exp. Med.* 185(7):1327–1335 (1997).
Linsley, P.S., "Distinct Roles for CD28 and Cytotoxic Lymphocyte–Associated Molecule–4 Receptors During T Cell Activation," *J. Exp. Med.*, 182:289–292 (1995).
Damle et al., "Costimulation of T Lymphocytes with Intergrin Ligands Intercellular Adhesion Molecule–1 or Vascular Cell Adhesion Molecule–1 Induces Functional Expression of CTLA–4, A Second Receptor for B7," *Journal of Immunology* 152:2686–2697 (1994).
Lin et al., "Long–Term Acceptance of Major Histocompatibility Complex Mismatched Cardiac Allografts Induced by CTLA4lg Plus Donor–Specific Transfusion," *J. Exp. Med.* 178:1801–1806 (1993).
Turka et al., "T–Cell Activation by the CD28 Ligand B7 is Required for Cardiac Allograft Rejection in vivo," *Proc. Natl. Acad. Sci. USA* 89:11102–11105 (1992).
Linsley, P.S. and J.A. Ledbetter, "The Role of the CD28 Receptor During T Cell Responses to Antigen," *Ann. Rev. Immunol.* 11:191–212 (1993).
Chen et al. (1992) *Cell* 71:1093–1102.
Walunas et al. (1994) *Immunity* 1:405–413.
Lenschow et al. (1992) *Science* 257:789–792.
Linsley et al. (1992) *Science* 257:792–795.
Lenschow et al. (1993) *P.N.A.S.* 90:11054–11058.
Freeman et al. (1993) *Science* 262:907–909.
Linsley et al. (1991) *J. Exp. Med.* 174:561–569.
Brunet et al. (1987) *Nature* 328:267–270.
Harding et al. (1994) *Nature* 356: 607–609.
Schwartz (1992) *Cell* 71:1065.
Townsend and Allison (1993) *Science* 259:368.
Linsley et al. (1992) *J. Exp. Med.* 176:1595–1604.
Gribben et al. (1995) *P.N.A.S.* 92:811–815.
Jenkins (1994) *Immunity* 1:443–446.
Bluestone (1995) *Immunity* 2:555–559.
June et al. (1994) *Immunology Today* 15:321–331.

*Primary Examiner*—Toni R. Scheiner
*Attorney, Agent, or Firm*—Flehr Hohbach Test Albritton & Herbert LLP

[57] ABSTRACT

T cell activation in response to antigen is increased by the administration of binding agents that block CTLA-4 signaling. When CTLA-4 signaling is thus blocked, the T cell response to antigen is released from inhibition. Such an enhanced response is useful for the treatment of tumors, chronic viral infections, and as an adjuvant during immunization.

12 Claims, 9 Drawing Sheets

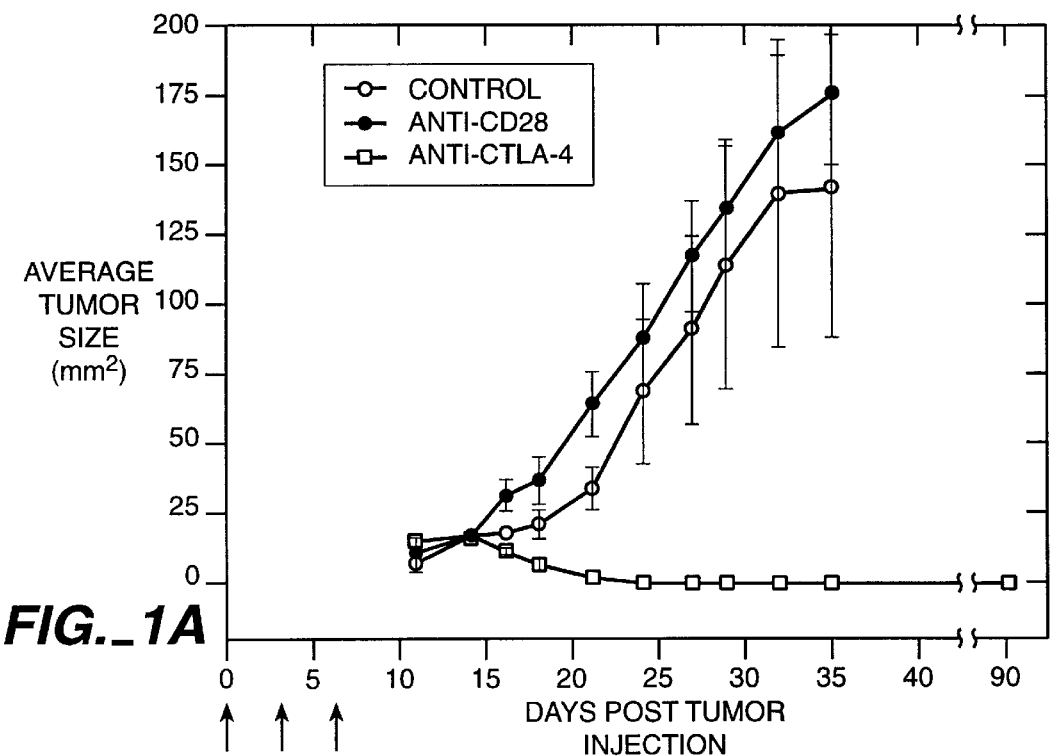
FIG._1A
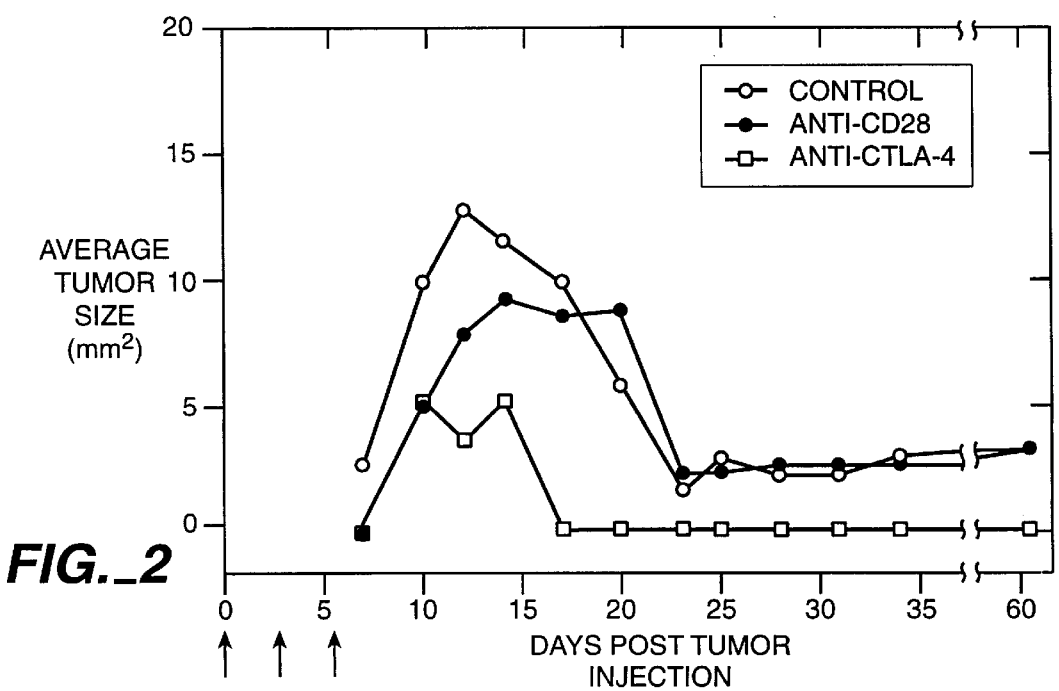
FIG._2

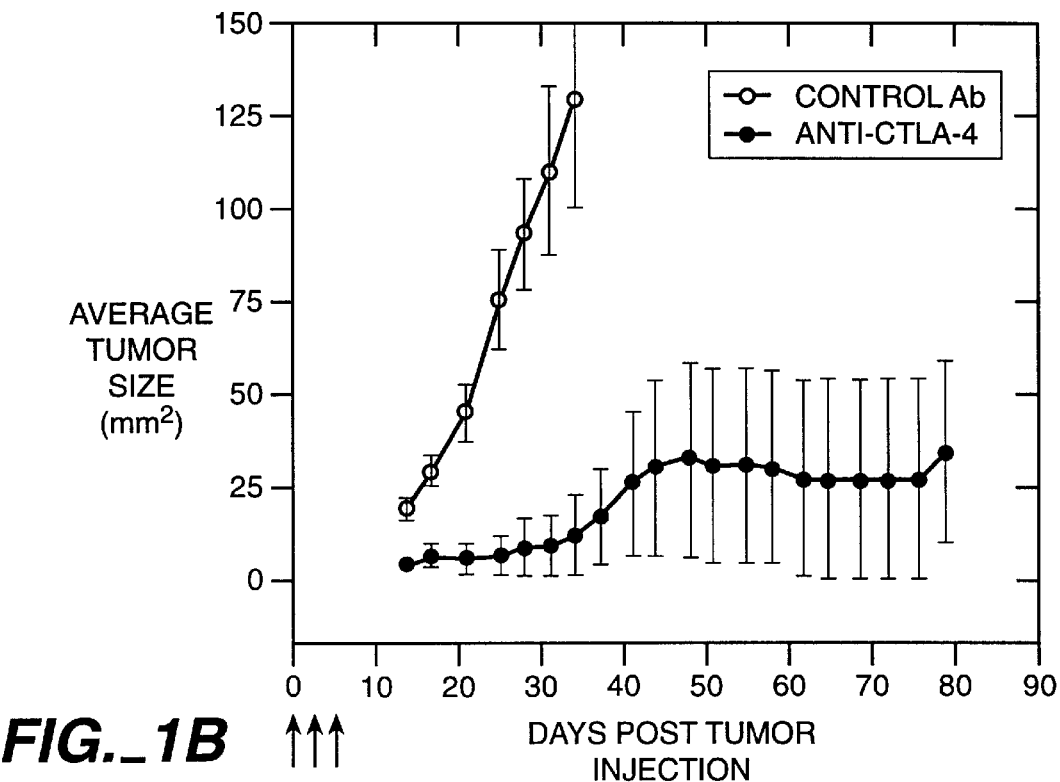
FIG._1B
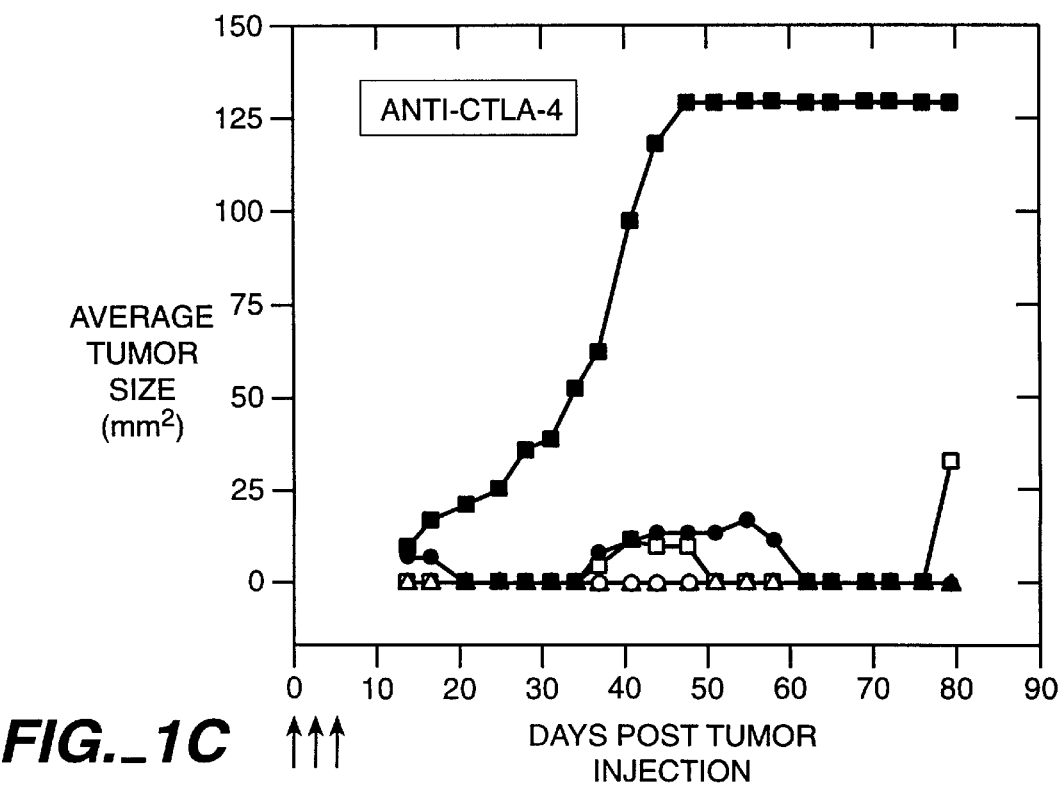
FIG._1C

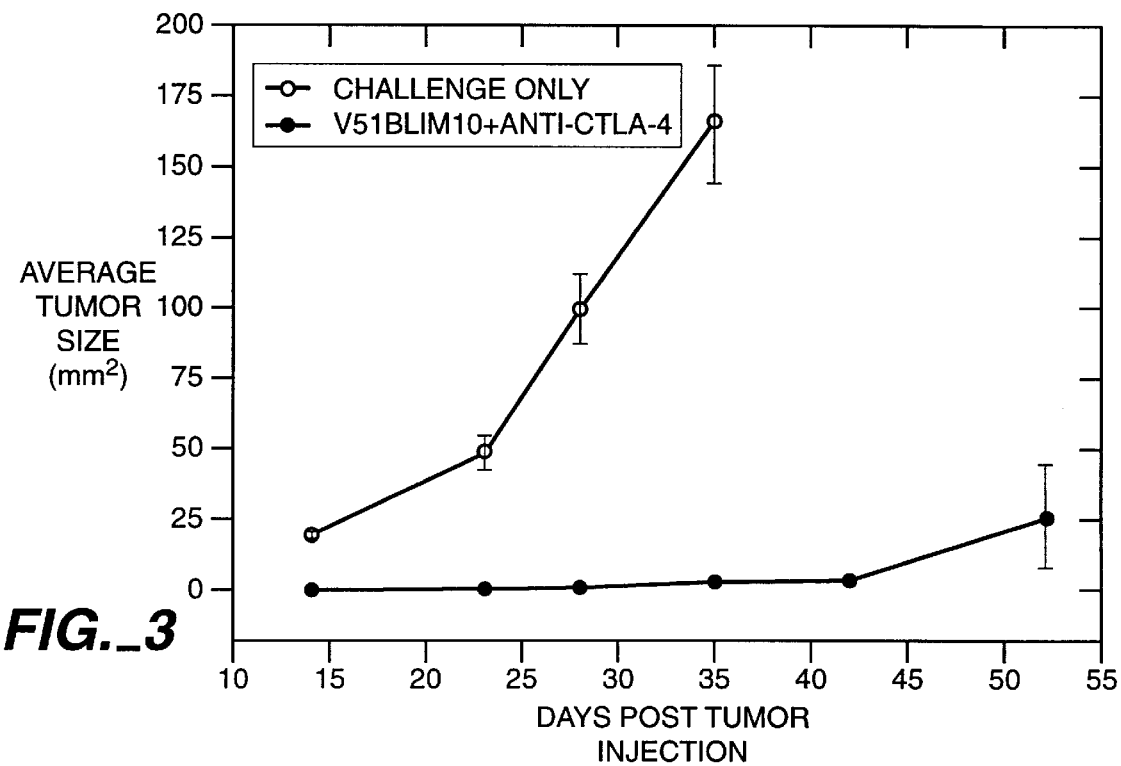
FIG._3
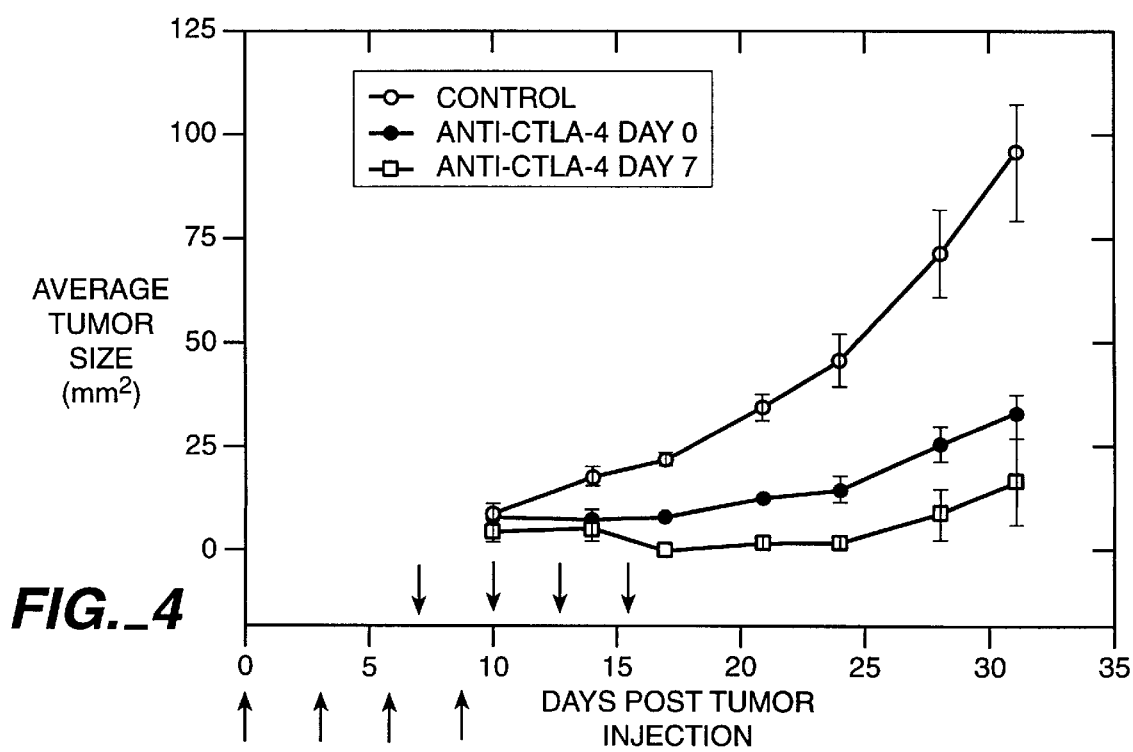
FIG._4

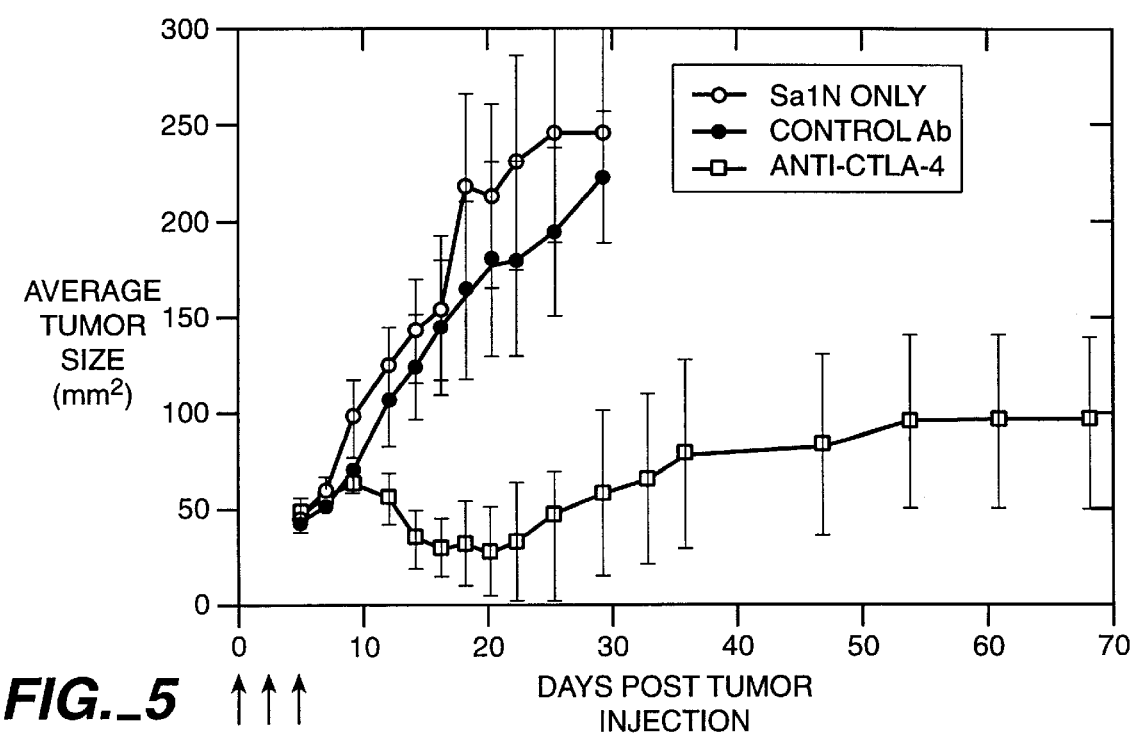
FIG._5

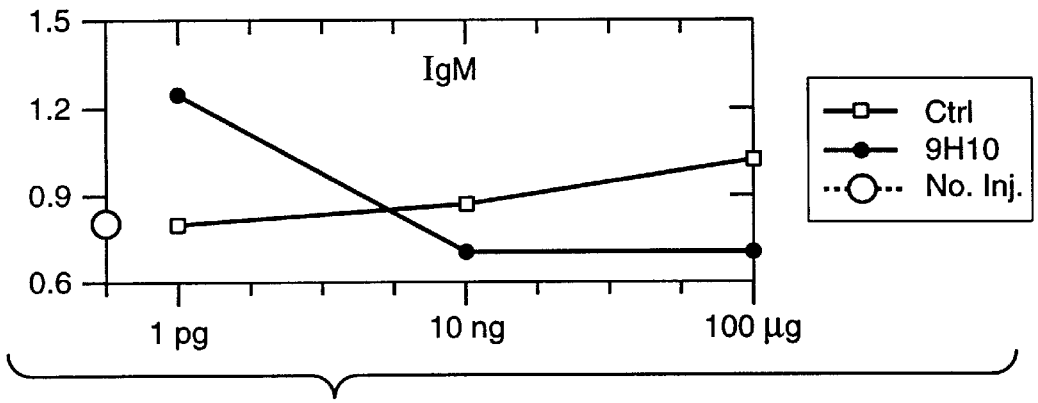
FIG._6A
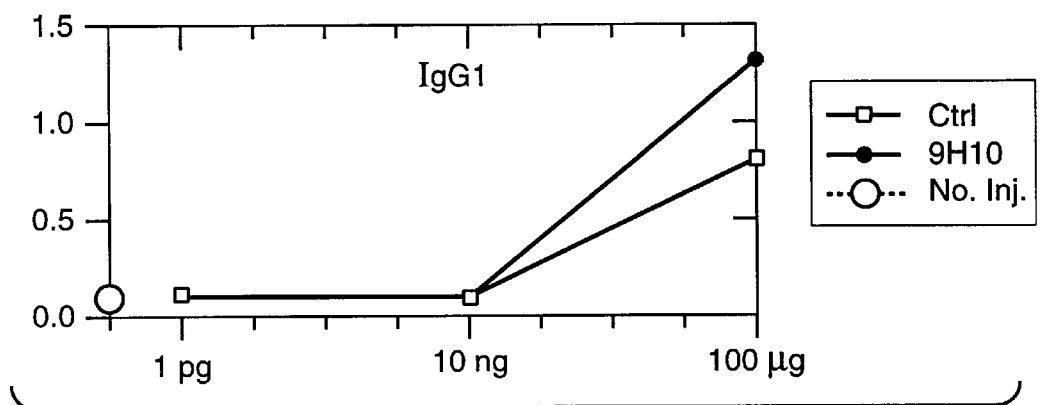
FIG._6B
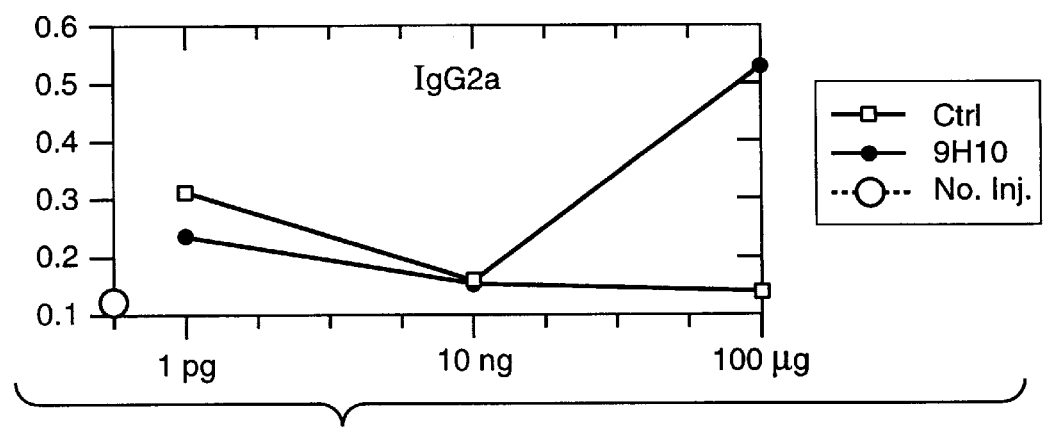
FIG._6C

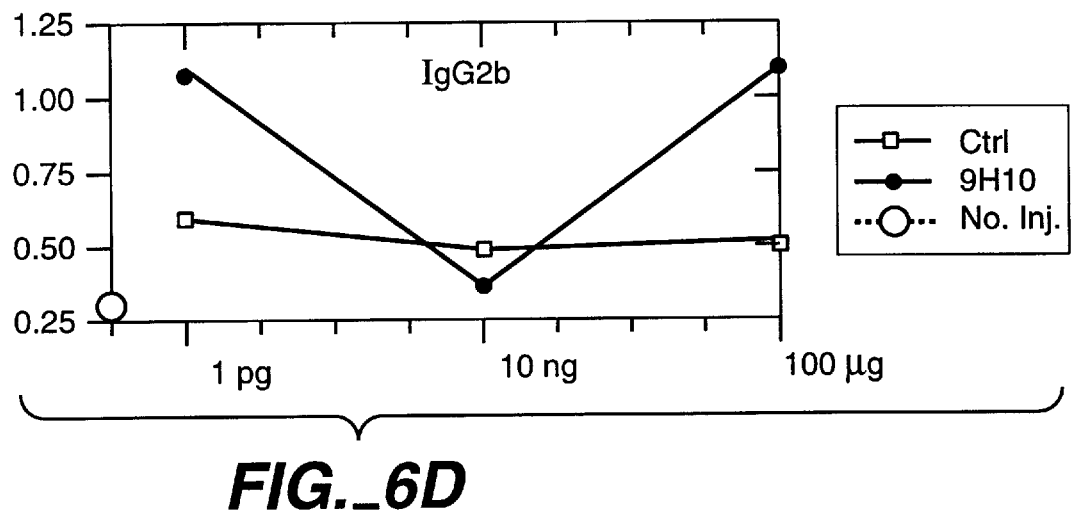
FIG._6D
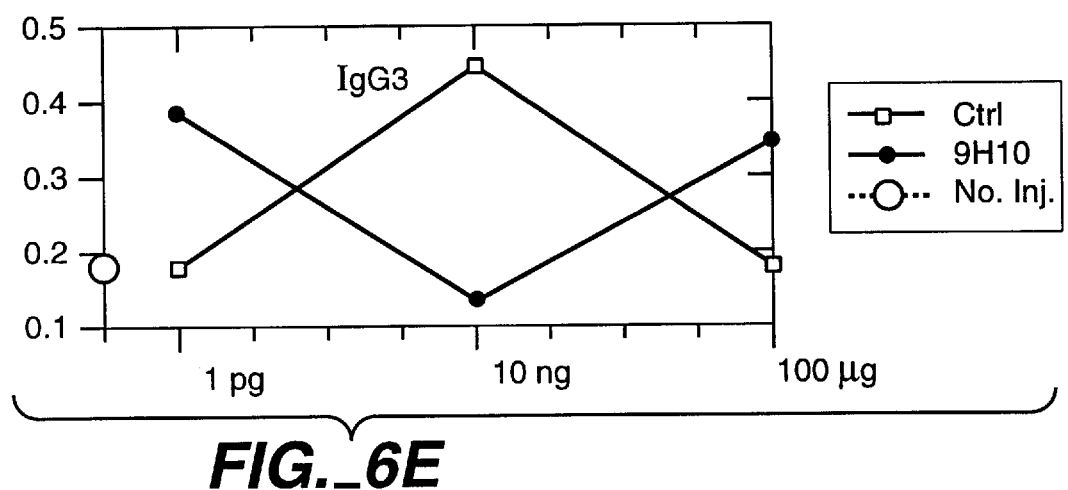
FIG._6E

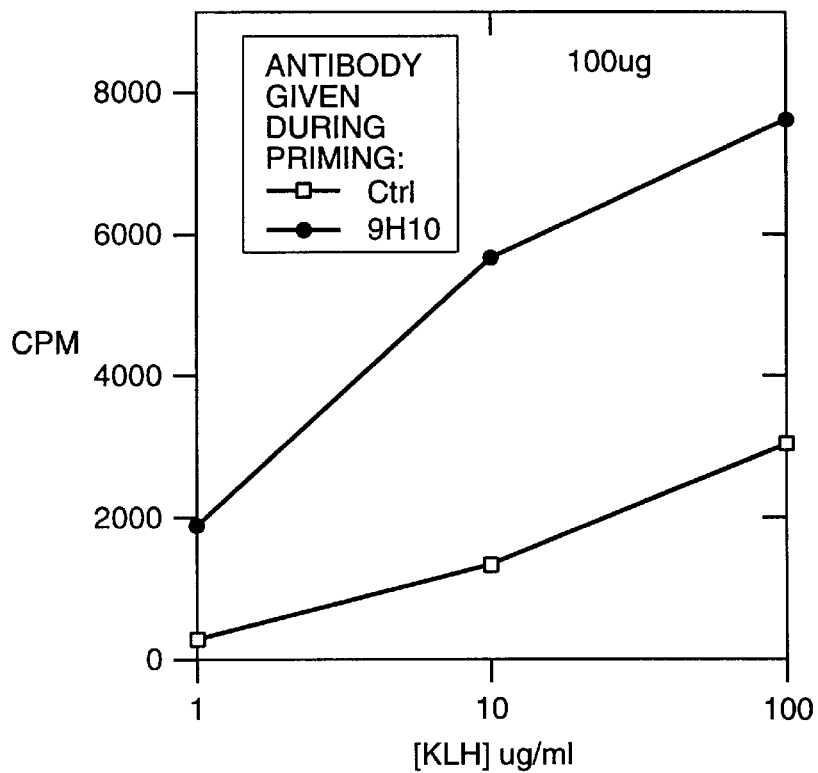
FIG._7A
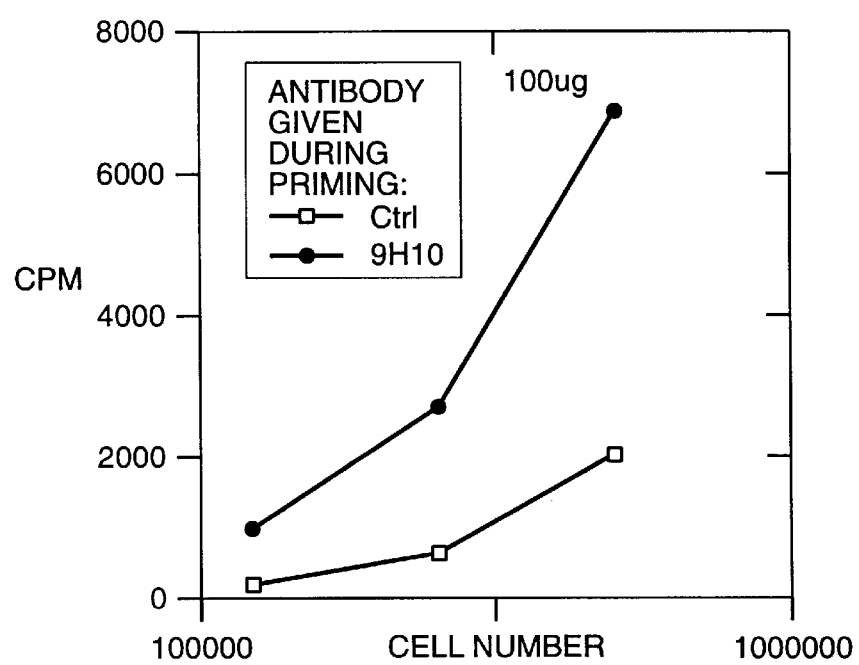
FIG._7B

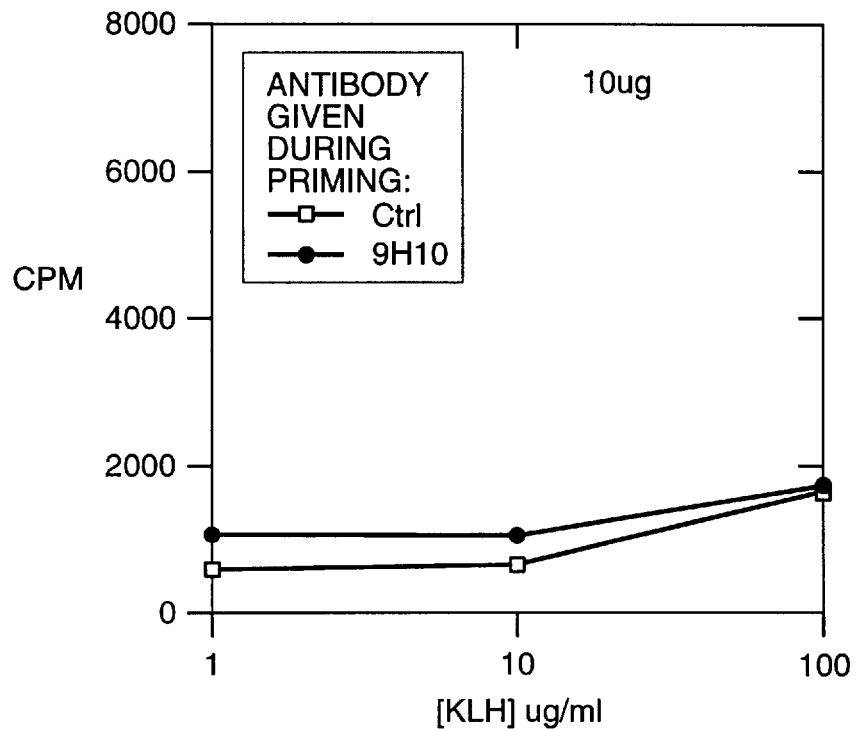
FIG._7C
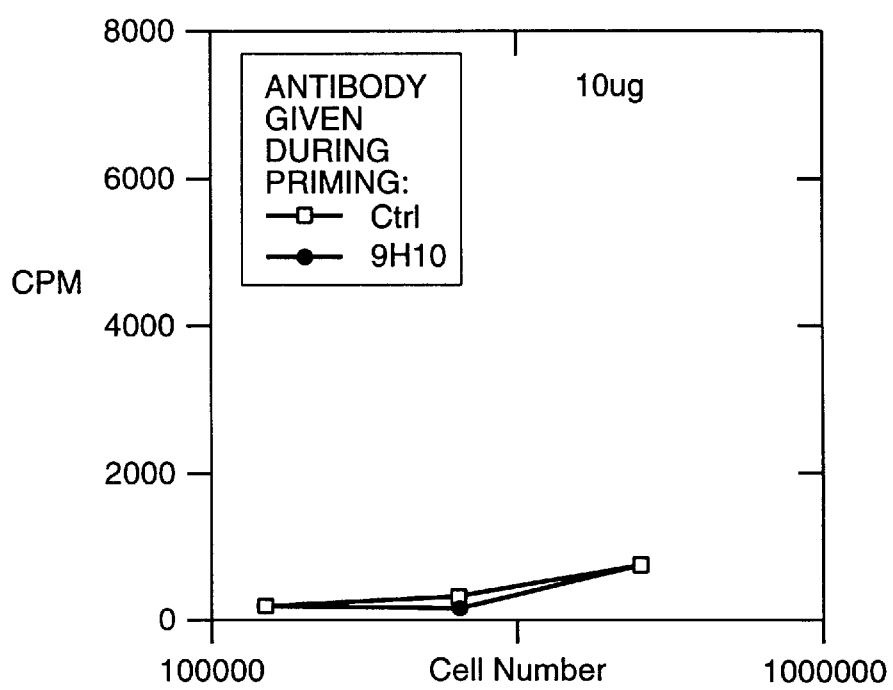
FIG._7D

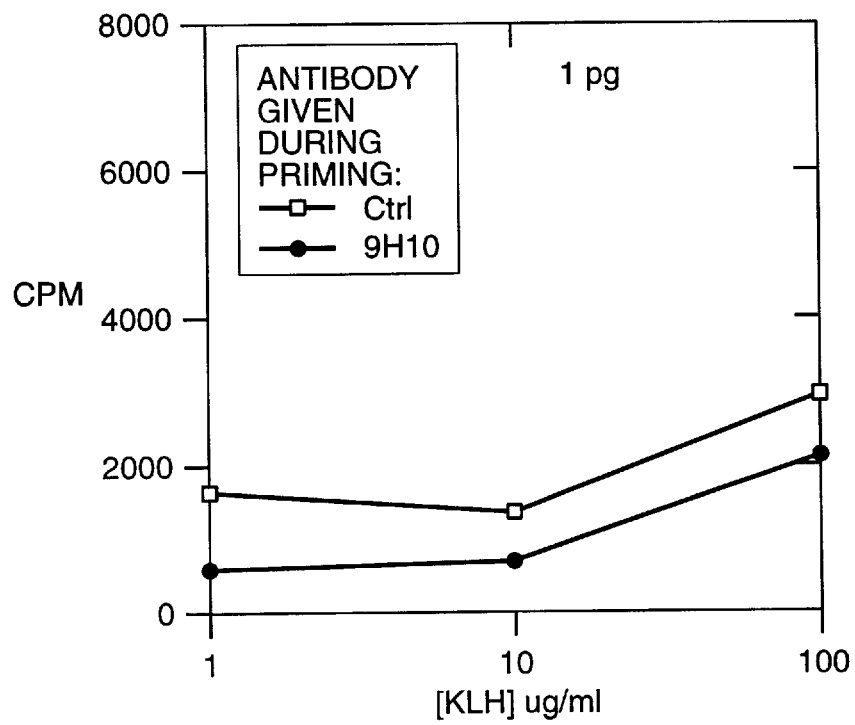
FIG._7E
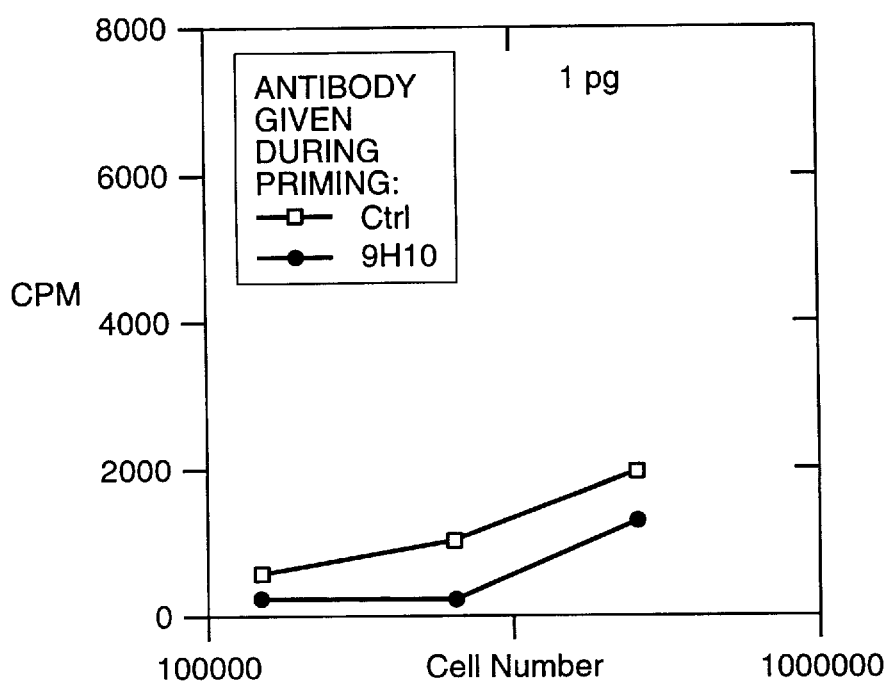
FIG._7F

BLOCKADE OF LYMPHOCYTE DOWN-REGULATION ASSOCIATED WITH CTLA-4 SIGNALING

CROSS-REFERENCE TO RELATED APPLICATIONS

This application is a continuation-in-part of U.S. patent application Ser. No. 08/506,666, filed Jul. 25, 1995, now abandoned.

This invention was made with government support under Contract Nos. CA 40041 and CA 09179 awarded by the National Institutes of Health. The Government has certain rights in this invention.

INTRODUCTION

Putting immunotherapy into practice is a highly desired goal in the treatment of human disease. It promises a specificity of action that is rarely found with the use of conventional drugs. The basis for immunotherapy is the manipulation of the immune response, particularly the responses of T cells. T cells possess complex and subtle systems for controlling their interactions, utilizing numerous receptors and soluble factors for the process. The effect that any particular signal will have on the immune response may vary, depending on the factors, receptors and counter-receptors that are involved.

The pathways for down-regulating responses are as important as those required for activation. Thymic education leading to T-cell tolerance is one mechanism for preventing an immune response to a particular antigen. Other mechanisms, such as secretion of suppressive cytokines, are also known.

Activation of T cells requires not only stimulation through the antigen receptor (TCR) but additional signaling through co-stimulatory surface molecules such as CD28. The ligands for CD28 are the B7-1 (CD80) and B72 (CD86) proteins, which are expressed on antigen-presenting cells such as dendritic cells, activated B-cells or monocytes. The interaction between B7 and CD28 is one of several co-stimulatory signaling pathways that appear to be sufficient to trigger the maturation and proliferation of antigen specific T-cells.

Lack of co-stimulation, and the concomitant inadequacy of IL-2 production, prevent subsequent proliferation of the T cell and induce a state of non-reactivity termed "energy". This is associated with a block in IL-2 gene transcription and a lack of responsiveness of the affected T cells to IL-4. Anergy may be overcome with prolonged IL-2 stimulation. A variety of viruses and tumors may block T cell activation and proliferation through direct or indirect means, thereby inducing a state of insufficient or non-reactivity of the host's immune system to infected or transformed cells. Among a number of functional T-cell disturbances, anergy may be at least partially responsible for the failure of the host to clear the pathogenic cells.

It would be advantageous if, in the treatment of infections and tumors, one could activate a strong cellular immune response through the manipulation of receptors involved in co-stimulation.

The use of B7 protein in mediating anti-tumor immunity is described in Chen et al. (1992) Cell 71:1093–1102 and Townsend and Allison (1993) Science 259:368. Schwartz (1992) Cell 71:1065 reviews the role of CD28, CTLA-4 and B7 in IL-2 production and immunotherapy. Harding et al. (1994) Nature 356:607–609 demonstrates that CD28 mediated signaling co-stimulates murine T cells and prevents the induction of anergy in T cell clones.

CTLA-4 is a T cell surface molecule that was originally identified by differential screening of a murine cytolytic T cell cDNA library, Brunet et al. (1987) Nature 328:267–270. The role of CTLA-4 as a second receptor for B7 is discussed in Linsley et al. (1991) J. Exp. Med. 174:561–569. Freeman et al. (1993) Science 262:907–909 discusses CTLA-4 in B7 deficient mice. Ligands for CTLA-4 are described in Lenschow et al. (1993) P.N.A.S. 90:11054–11058.

Linsley et al. (1992) Science 257:792–795 describes immunosuppression in vivo by a soluble form of CTLA-4. Lenschow et aL (1992) Science 257:789–792 discusses long term survival of pancreatic islet grafts induced by CTLA-41g. It is suggested in Walunas et al. (1994) Immunity 1:405–413, that CTLA-4 can function as a negative regulator of T cell activation.

SUMMARY OF THE INVENTION

Methods and compositions are provided for increasing the activation of T cells through a blockade of CTLA-4 signaling. Binding molecules that specifically interact with the CTLA-4 antigen, but do not activate signaling (blocking agents), are combined with T cells, in vitro or in vivo. When CTLA-4 signaling is thus blocked, the T cell response to antigen is released from inhibition. Such an enhanced response is useful for the treatment of tumors, chronic viral infections, and as an adjuvant during immunization.

BRIEF DESCRIPTION OF THE DRAWINGS

FIG. 1A is a graph illustrating the in vivo growth of the tumor cell line V51Blim10 in the presence or absence of antibodies directed against CTLA-4 or CD28. FIG. 1B is a graph illustrating the average tumor size in mice injected with $2 \times 10^6$ V51Blim10 cells and antibodies. FIG. 1C is a graph illustrating individual tumor growth size in mice injected with V51Blim10 cells.

FIG. 2 is a graph showing the in vivo growth of B7-51BL10 tumors in the presence or absence of antibodies directed against CTLA-4 or CD28.

FIG. 3 shows the rejection of wild-type colon carcinoma cells by mice previously treated with V51BLim10 cells and anti-CTLA-4 antibody.

FIG. 4 shows the growth of established tumors after treatment with anti-CTLA-4 antibody.

FIG. 5 shows the growth of the murine firbosarcoma SA1N in the absence or presence of anti-CTLA-4 antibodies.

FIGS. 6A to 6E illustrate the adjuvant effect of anti-CTLA-4 antibodies in the response of T cells to peptide antigens.

FIGS. 7A to 7F illustrate the effect of CTLA-4 blockade on class switching.

DATABASE REFERENCES FOR NUCLEOTIDE AND AMINO ACID SEQUENCES

The complete cDNA sequence of human CTLA-4 has the Genbank accession number L15006. The region of amino acids 1–37 is the leader peptide; 38–161 is the extracellular V-like domain; 162–187 is the transmembrane domain; and 188–223 is the cytoplasmic domain. Variants of the nucleotide sequence have been reported, including a G to A transition at position 49, a C to T transition at position 272, and an A to G transition at position 439. The complete DNA sequence of mouse CTLA-4 has the EMBL accession number X05719 (Brunet et aL (1987) Nature 328:267–270). The region of amino acids 1–35 is the leader peptide.

The complete DNA sequence of human B7-1 (CD80) has the Genbank accession number X60958; the accession number for the mouse sequence is X60958; the accession number for the rat sequence is U05593. The complete cDNA sequence of human B7-2 (CD86) has the Genbank accession number L25259; the accession number for the mouse sequence is L25606.

The genes encoding CD28 have been extensively characterized. The chicken mRNA sequence has the Genbank accession number X67915. The rat mRNA sequence has the Genbank accession number X55288. The human mRNA sequence has the Genbank accession number J02988. The mouse mRNA sequence has the Genbank accession number M34536.

DETAILED DESCRIPTION OF THE INVENTION

Methods and compositions are provided for up-regulating the response of T cells to antigenic stimulation. Binding molecules that specifically interact with cell surface CTLA-4, but do not activate CTLA-4 signaling (blocking agents), are combined with T cells. The T cell response to antigen is increased in the presence of the blocking agents. Such treatment is useful for increasing the specific immune response against tumors, chronic pathogenic infections, and as an adjuvant during immunization.

It is not necessary for the practice of the invention that the mechanism of action be understood. The data indicate that the subject therapy releases T cells from inhibitory signals mediated through CTLA-4. The T cell response to antigen and co-stimulatory CD28 signaling is thereby upregulated in the presence of CTLA-4 blocking agents. The subject methods do not promote a generalized proliferation of unstimulated T cells.

The subject methods are useful where there is an inadequate T cell mediated response to an antigenic stimulus for an intended purpose. In vivo T cell mediated responses include the generation of cytolytic T cells, and the majority of antibody responses, particularly those involving class switching of immunoglobulin isotypes. The antigenic stimulus may be the presence of viral antigens on infected cells; tumor cells that express proteins or combinations of proteins in an unnatural context; parasitic or bacterial infection; or an immunization, e.g. vaccination, preparing monoclonal antibodies, etc. In vitro, the subject methods are used to increase the response of cultured T cells to antigen. Such activated T cells find use in adoptive immunotherapy, to study the mechanisms of activation, in drug screening, etc.

CTLA-4 blocking agents are molecules that specifically bind to the extracellular domain of CTLA-4 protein, and block the binding of CTLA-4 to its counter-receptors, e.g. CD80, CD86, etc. Usually the binding affinity of the blocking agent will be at least about 100 $\mu$M. The blocking agent will be substantially unreactive with related molecules to CTLA-4, such as CD28 and other members of the immunoglobulin superfamily. Molecules such as CD80 and CD86 are therefore excluded as blocking agents. Further, blocking agents do not activate CTLA-4 signaling. Conveniently, this is achieved by the use of monovalent or bivalent binding molecules. It will be understood by one of skill in the art that the following discussions of cross-reactivity and competition between different molecules is intended to refer to molecules having the same species of origin, e.g. human CTLA-4 binds human CD80 and 86, etc.

Candidate blocking agents are screened for their ability to meet this criteria. Assays to determine affinity and specificity of binding are known in the art, including competitive and non-competitive assays. Assays of interest include ELISA, RIA, flow cytometry, etc. Binding assays may use purified or semi-purified CTLA-4 protein, or alternatively may use T cells that express CTLA-4, e.g. cells transfected with an expression construct for CTLA-4; T cells that have been stimulated through cross-linking of CD3 and CD28; the addition of irradiated allogeneic cells, etc. As an example of a binding assay, purified CTLA-4 protein is bound to an insoluble support, e.g. microtiter plate, magnetic beads, etc. The candidate blocking agent and soluble, labeled CD80 or CD86 are added to the cells, and the unbound components are then washed off. The ability of the blocking agent to compete with CD80 and CD86 for CTLA-4 binding is determined by quantitation of bound, labeled CD80 or CD86. Confirmation that the blocking agent does not cross-react with CD28 may be performed with a similar assay, substituting CD28 for CTLA-4. Suitable molecules will have at least about $10^3$ less binding to CD28 than to CTLA-4, more usually at least about $10^4$ less binding.

Generally, a soluble monovalent or bivalent binding molecule will not activate CTLA-4 signaling. A functional assay that detects T cell activation may be used for confirmation. For example, a population of T cells may be stimulated with irradiated allogeneic cells expressing CD80 or CD86, in the presence or absence of the candidate blocking agent. An agent that blocks CTLA-4 signaling wil cause an increase in the T cell activation, as measured by proliferation, release of IL-2, etc. It will be understood by one of skill in the art that expression on the surface of a cell, packaging in a liposome, adherence to a particle or well, etc. will increase the effective valency of a molecule.

Blocking agents are peptides, small organic molecules, peptidomimetics, soluble T cell receptors, antibodies, or the like. Antibodies are a preferred blocking agent. Antibodies may be polyclonal or monoclonal; intact or truncated, e.g. F(ab')$_2$, Fab, Fv; xenogeneic, allogeneic, syngeneic, or modified forms thereof, e.g. humanized, chimeric, etc.

In many cases, the blocking agent will be an oligopeptide, e.g. antibody or fragment thereof, etc., but other molecules that provide relatively high specificity and affinity may also be employed. Combinatorial libraries provide compounds other than oligopeptides that have the necessary binding characteristics. Generally, the affinity will be at least about 10–6, more usually about $10^-$M, i.e. binding affinities normally observed with specific monoclonal antibodies.

A number of screening assays are available for blocking agents. The components of such assays will typically include CTLA-4 protein; and optionally a CTLA-4 activating agent, e.g. CD80, CD86, etc. The assay mixture will also comprise a candidate pharmacological agent. Generally a plurality of assay mixtures are run in parallel with different agent concentrations to obtain a differential response to the various concentrations. Typically, one of these concentrations serves as a negative control, i.e. at zero concentration or below the level of detection.

Conveniently, in these assays one or more of the molecules will be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which provides for detection, in accordance with known procedures.

One screening assay of interest is directed to agents that interfere with the activation of CTLA-4 by its counter-receptors. Quantitation of activation may be achieved by a number of methods known in the art. For example, the inhibition of T cell activation may be determined by quantitating cell proliferation, release of cytokines, etc.

Other assays of interest are directed to agents that block the binding of CTLA-4 to its counter-receptors. The assay mixture will comprise at least a portion of the natural counter-receptor, or an oligopeptide that shares sufficient sequence similarity to provide specific binding, and the candidate pharmacological agent. The oligopeptide may be of any length amenable to the assay conditions and requirements, usually at least about 8 aa in length, and up to the full-length protein or fusion thereof. The CTLA-4 may be bound to an insoluble substrate. The substrate may be made in a wide variety of materials and shapes e.g. microtiter plate, microbead, dipstick, resin particle, etc. The substrate is chosen to minimize background and maximize signal to noise ratio. Binding may be quantitated by a variety of methods known in the art. After an incubation period sufficient to allow the binding to reach equilibrium, the insoluble support is washed, and the remaining label quantitated. Agents that interfere with binding will decrease the detected label.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl, sulfhydryl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

A variety of other reagents may be included in the screening assay. These include reagents like salts, neutral proteins, e.g. albumin, detergents, etc which may be used to facilitate optimal protein-DNA binding and/or reduce non-specific or background interactions. Also reagents that otherwise improve the efficiency of the assay, such as protease inhibitors, nuclease inhibitors, anti-microbial agents, etc. may be used.

Suitable antibodies for use as blocking agents are obtained by immunizing a host animal with peptides comprising all or a portion of CTLA-4 protein. Suitable host animals include mouse, rat, sheep, goat, hamster, rabbit, etc. The origin of the protein immunogen may be mouse, human, rat, monkey etc. The host animal will generally be a different species than the immunogen, e.g. mouse CTLA-4 used to immunize hamsters, human CTLA-4 to immunize mice, etc. The human and mouse CTLA-4 contain highly conserved stretches in the extracellular domain (Harper et aL (1991) *J. Immunol.* 147:1037–1044). Peptides derived from such highly conserved regions may be used as immunogens to generate cross-specific antibodies.

The immunogen may comprise the complete protein, or fragments and derivatives thereof. Preferred immunogens comprise all or a part of the extracellular domain of human CTLA-4 (amino acid residues 38–161), where these residues contain the post-translation modifications, such as glycosylation, found on the native CTLA-4. Immunogens comprising the extracellular domain are produced in a variety of ways known in the art, e.g. expression of cloned genes using conventional recombinant methods, isolation from T cells, sorted cell populations expressing high levels of CTLA-4, etc.

Where expression of a recombinant or modified protein is desired, a vector encoding the desired portion of CTLA-4 will be used. Generally, an expression vector will be designed so that the extracellular domain of the CTLA-4 molecule is on the surface of a transfected cell, or alternatively, the extracellular domain is secreted from the cell. When the extracellular domain is to be secreted, the coding sequence for the extracellular domain will be fused, in frame, with sequences that permit secretion, including a signal peptide. Signal peptides may be exogenous or native. A fusion protein of interest for immunization joins the CTLA-4 extracellular domain to the constant region of an immunoglobulin. For example, a fusion protein comprising the extracellular domain of mouse CTLA-4 joined to the hinge region of human Cγ1 (hinge-CH2–CH3) domain may be used to immunize hamsters.

When the CTLA-4 is to be expressed on the surface of the cell, the coding sequence for the extracellular domain will be fused, in frame, with sequences encoding a peptide that anchors the extracellular domain into the membrane and a signal sequence. Such anchor sequences include the native CTLA-4 transmembrane domain, or transmembrane domains from other cell surface proteins, e.g. CD4, CD8, sig, etc. Mouse cells transfected with the human CTLA-4 gene may be used to immunize mice and generate antibodies specific for the human CTLA-4 protein.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using CTLA-4 bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the blocking agent. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90104036). Alternatively, the antibody of interest may be engineered by recombinant DNA techniques to substitute the CH1, CH2, CH3, hinge domains, and/or the framework domain with the corresponding human sequence (see WO 92102190).

The use of Ig cDNA for construction of chimeric immunoglobulin genes is known in the art (Liu et al. (1987) P.N.A.S. 84:3439 and (1987) J. I. Immunol. 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683, 202). Alternatively, a library is made and screened to isolate the sequence of interest. The DNA sequence encoding the variable region of the antibody is then fused to human constant region sequences. The sequences of human constant regions genes may be found in Kabat et aL (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgGi, lgG3 and lgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) Mol. Cell. Bio. 3:280), Rous sarcoma virus LTR (Gorman et al. (1982) P.N.A.S. 79:6777), and moloney murine leukemia virus LTR (Grosschedl et al. (1985) Cell 41:885); native Ig promoters, etc.

Situations characterized by deficient host T cell response to antigen include chronic infections, tumors, immunization with peptide vaccines, and the like. Administration of the subject CTLA-4 blockers to such hosts specifically changes the phenotype of activated T cells, resulting in increased response to antigen mediated activation. Treatment of primates, more particularly humans is of interest, but other mammals may also benefit from treatment, particularly domestic animals such as equine, bovine, ovine, feline, canine, murine, lagomorpha, and the like.

The formulation is administered at a dose effective to increase the response of T cells to antigenic stimulation. The response of activated T cells will be affected by the subject treatment to a greater extent than resting T cells. The determination of the T cell response will vary with the condition that is being treated. Useful measures of T cell activity are proliferation, the release of cytokines, e.g. IL-2, IFN$_\gamma$, TNF$_\alpha$; and other measures of T cell activity as known in the art.

The subject treatment may be performed in combination with administration of cytokines that stimulate antigen presenting cells, e.g. granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), etc. Additional proteins and/or cytokines known to enhance T cell proliferation and secretion, such as IL-1, IL-2, B7, anti-CD3 and anti-CD28 can be employed simultaneously or sequentially with the blocking agents to augment the immune response. The subject therapy may be combined with the transfection of tumor cells or tumor-infiltrating lymphocytes with genes encoding for various cytokines or cell surface receptors (see Ogasawara et al. (1993) Cancer Res. 53:3561–8; and Townsend et al. (1993) Science 259:368–370). For example, it has been shown that transfection of tumor cells with cDNA encoding CD80 leads to rejection of transfected tumor cells, and can induce immunity to a subsequent challenge by the non-transfected parent tumor cells (Townsend et al. (1994) Cancer Res. 54:6477–6483). The subject therapy enhances this effect.

Tumor-specific host T cells may be combined ex vivo with the subject blocking agents, and tumor antigens or cells and reinfused into the patient. When administered to a host, the stimulated cells induce a tumoricidal reaction resulting in tumor regression. The host cells may be isolated from a variety of sources, such as lymph nodes, e.g. inguinal, mesenteric, superficial distal auxiliary, etc.; bone marrow; spleen; or peripheral blood, as well as from the tumor, e.g. tumor infiltrating lymphocytes. The cells may be allogeneic or, preferably, autologous. For ex vivo stimulation, the host cells are aseptically removed, and are suspended in any suitable media, as known in the art. The cells are stimulated by any of a variety of protocols, particularly combinations of B7, anti-CD28, etc., in combination with the blocking agents. The stimulated cells are reintroduced to the host by injection, e.g. intravenous, intraperitoneal, etc. in a variety of pharmaceutical formulations, including such additives as binder, fillers, carriers, preservatives, stabilizing agents, emulsifiers and buffers. Suitable diluents and excipients are water, saline, glucose and the like.

Tumor cells whose growth may be decreased by administration of the subject blocking agents include carcinomas e.g. adenocarcinomas, which may have a primary tumor site in the breast, ovary, endometrium, cervix, colon, lung, pancreas, eosophagus, prostate, small bowel, rectum, uterus or stomach; and squamous cell carcinomas, which may have a primary site in the lungs, oral cavity, tongue, larynx, eosophagus, skin, bladder, cervix, eyelid, conjunctiva, vagina, etc. Other classes of tumors that may be treated include sarcomas, e.g. myogenic sarcomas; neuromas; melanomas; leukemias, certain lymphomas, trophoblastic and germ cell tumors; neuroendocrine and neuroectodermal tumors.

Tumors of particular interest are those that present tumor-specific antigens. Such antigens may be present in an abnormal context, at unusually high levels, or may be mutated forms. The tumor antigen may be administered with the subject blocking agents to increase the host T cell response against the tumor cells. Such antigen preparations may comprise purified protein, or lysates from tumor cells.

Examples of tumors antigens are cytokeratins, particularly cytokeratin 8, 18 and 19, as an antigen for carcinomas. Epithelial membrane antigen (EMA), human embryonic antigen (HEA-125); human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. Chromagranin-A and synaptophysin are antigens of neuroendocrine and neuroectodermal tumors. Of particular interest are aggressive tumors that form solid tumor masses having necrotic areas. The lysis of such necrotic cells is a rich source of antigens for antigen-presenting cells.

Administration of the subject blocking agents may be contra-indicated for certain lymphomas. In particular, T cell lymphomas may not benefit from increased activation. CD80 antigen is strongly expressed by the Reed-Sternberg cells in Hodgkin's disease, which are frequently surrounded by CD28-expressing T cells (Delabie et al. (1993) *Blood* 82:2845–52). It has been suggested that the accessory cell function of Reed-Sternberg cells leads to T cell activation, and contributes to the Hodgkin's syndrome.

Many conventional cancer therapies, such as chemotherapy and radiation therapy, severely reduce lymphocyte populations. While the subject therapy may alleviate this immunosuppression to some extent, a preferred course of combined treatment will use such lymphotoxic therapies before or after the subject therapy.

The subject blocking agents may be administered to increase the response of T cells to pathogens. Infections with certain viruses become chronic when the host anti-viral mechanisms fail. Such infections can persist for many years or even the life-time of the infected host, and often cause serious disease. Chronic infections associated with significant morbidity and early death include those with two human hepatitis viruses, hepatitis B virus (HBV) and hepatitis C virus (HCC), which cause chronic hepatitis, cirrhosis and liver cancer. Other chronic viral infections in man include those with human retroviruses: human immunodeficiency viruses (HIV-1 and HIV-2) which cause AIDS and human T lymphotropic viruses (HTLV-1 and HTLV-2) which cause T cell leukemia and myelopathies. Infections with human herpes viruses including herpes simplex virus (HSV) types 1 and 2, Epstein Barr virus (EBV), cytomegalovirus (CMV) varicella-zoster virus (VZV) and human herpes virus 6 (HHV-6) are usually not eradicated by host mechanisms. Infection with other agents that replicate intracellularly, such as pathogenic protozoa, e.g. trypanosomes, malaria and toxoplasma gondii; bacteria, e.g. mycobacteria, salmonella and listeria; and fungi, e.g. candida; may also become chronic when host defense mechanisms fail to eliminate them.

The subject blocking agents are administered to a patient suffering from such a chronic pathogen infection. To increase the immune response, it may be desirable to formulate the blocking agent with antigens derived from the pathogen. A variety of such antigens are known in the art, and available by isolation of the pathogen or expression by recombinant methods. Examples include HIV gp 120, HBV surface antigen, envelope and coat proteins of viruses, etc.

Adjuvants potentiate the immune response to an antigen. The CTLA-4 blocking agents are used as an adjuvant to increase the activation of T cells, and to increase the class switching of antibody producing cells, thereby increasing the concentration of IgG class antibodies produced in response to the immunogen. The blocking agents are combined with an immunogen in a physiologically acceptable medium, in accordance with conventional techniques for employing adjuvants. The immunogen may be combined in a single formulation with the blocking agent, or may be administered separately. Immunogens include polysaccharides, proteins, protein fragments, haptens, etc. Of particular interest is the use with peptide immunogens. Peptide immunogens may include tumor antigens and viral antigens or fragments thereof, as described above.

The use of the subject blocking agents in conjunction with genetic immunization is also of interest. A DNA expression vector encoding a peptide or protein antigen of interest is injected into the host animal, generally in the muscle or skin. The gene products are correctly glycosylated, folded and expressed by the host cell. The method is advantageous where the antigens are difficult to obtain in the desired purity, amount or correctly glycosylated form or when only the genetic sequences are known e.g. HCV. Typically, DNA is injected into muscles or delivered coated onto gold microparticles into the skin by a particle bombardment device, a "gene gun". Genetic immunization has demonstrated induction of both a specific humoral but also a more broadly reacting cellular immune response in animal models of cancer, mycoplasma, TB, malaria, and many virus infections including influenza and HIV. See, for example, Mor et al. (1995) *J Immunol* 155:2039–46; Xu and Liew (1995) Immunology 84:173–6; and Davis et al. (1994) Vaccine 12:1503–9.

The subject blocking agents are used during the immunization of laboratory animals, e.g. mice, rats, hamsters, rabbits, etc. for monoclonal antibody production. The administration increases the level of response to the antigen, and increases the proportion of plasma cells that undergo class switching.

CTLA-4 blockers are administered in vitro to increase the activation of T cells in culture, including any in vitro cell culture system, e.g. immortalized cell lines, primary cultures of mixed or purified cell populations, non-transformed cells, etc. Of particular interest are primary T cell cultures, where the cells may be removed from a patient or allogeneic donor, stimulated ex vivo, and reinfused into the patient.

Various methods for administration may be employed. The CTLA-4 blocking agent formulation may be injected intravascularly, subcutaneously, peritoneally, etc. The dosage of the therapeutic formulation will vary widely, depending upon the nature of the disease, the frequency of administration, the manner of administration, the purpose of the administration, the clearance of the agent from the host, and the like. The dosage administered will vary depending on known factors, such as the pharmacodynamic characteristics of the particular agent, mode and route of administration, age, health and weight of the recipient, nature and extent of symptoms, concurrent treatments, frequency of treatment and effect desired. The dose may be administered as infrequently as weekly or biweekly, or fractionated into smaller doses and administered daily, semi-weekly, etc. to maintain an effective dosage level. Generally, a daily dosage of active ingredient can be about 0.1 to 100 mg/kg of body weight. Dosage forms suitable for internal administration generally contain from about 0.1 mg to 500 mgs of active ingredient per unit. The active ingredient may vary from 0.5 to 95% by weight based on the total weight of the composition.

In some cases it may be desirable to limit the period of treatment due to excessive T cell proliferation. The limitations will be empirically determined, depending on the response of the patient to therapy, the number of T cells in the patient, etc. The number of T cells may be monitored in a patient by methods known in the art, including staining with T cell specific antibodies and flow cytometry.

The subject CTLA-4 blockers are prepared as formulations at an effective dose in pharmaceutically acceptable media, for example normal saline, vegetable oils, mineral oil, PBS, etc. Therapeutic preparations may include physiologically tolerable liquids, gel or solid carriers, diluents, adjuvants and excipients. Additives may include bactericidal agents, additives that maintain isotonicity, e.g. NaCI, mannitol; and chemical stability, e.g. buffers and preservatives. or the like. The CTLA-4 blockers may be administered as a cocktail, or as a single agent. For parenteral administration, the blocking agent may be formulated as a solution, suspension, emulsion or lyophilized powder in association with a pharmaceutically acceptable parenteral vehicle. Liposomes or non-aqueous vehicles, such as fixed oils, may also be used. The formulation is sterilized by techniques as known in the art.

The functional effect of CTLA-4 blockade may also be induced by the administration of other agents that mimic the change in intra-cellular signaling observed with the subject invention. For example, it is known that specific cytoplasmic kinases may be activated in response to binding of extracellular receptors. Agents that block the kinase activity would have a similar physiological effect as blocking receptor binding. Similarly, agents that increase cyclic AMP, GTP concentrations and intracellular calcium levels can produce physiological effects that are analagous to those observed with extracellular receptor binding.

The following examples are offered by way of illustration and not by way of limitation.

EXPERIMENTAL

EXAMPLE 1

Generation of Monoclonal Antibodies Reactive With Mouse CTLA-4 a) Preparation of a Mouse CTLA-4 Immunogen

A fusion protein comprising the extracellular portions of the mouse CTLA-4 gene and the constant region of human IgGI, termed mCTLA4-Hγ1, was obtained from Drs. P. Lane and K. Karjalainen (Basel Institute for Immunology, Basel, Switzerland). An expression vector capable of expressing the mCTLA4-Hλ1 protein was constructed as described [Lane, et al. Immunol. 80:56 (1993)]. Briefly, sequences encoding the extracellular portions of the mouse CTLA-4 molecule were generated using PCR. The following primer pair was used to amplify these CTLA-4 sequences from a plasmid containing mouse CTLA-4 sequences: 5'-TTACTCTACTCCCTGAGG AGCTCAGCACATTTGCC-3' (SEQ ID NO:1) and 5'-TATACTTACCAGAATCCG GGCATGGTTCTGGATCA-3' (SEQ ID NO:2). The amplified CTLA-4 sequences were then inserted into an expression vector that permits the insertion of a gene of interest upstream of sequences encoding the hinge, CH2 and CH3 domains of the human IgG1 protein [Traunecker, et al. Trends Biotech. 9:109 (1991)]. Each primer contained appropriate restriction sites for subcloning into the human IgG1 expression vector, together with a 3' splice donor site within the 3' primer to splice to the human γ1 exons correctly. The plasmid containing sequences encoding the mCTLA-4-Hγ1 fusion protein was termed pH β-APr-1-neo-mCTLA4-Hγ1. The amino acid sequence of the mCTLA4-Hγ1 protein is listed in SEQ ID NO:3.

To express the mCTLA4-Hγ1 protein, the pβAPr-l-neo-mCTLA4-Hγ1 expression vector was transfected into the mouse plasmacytoma line, J558L (J558L is identical to the J558 cell line which is available from ATCC [ATCC TIB 6]) using the standard technique of protoplast fusion. J558L cells were cultured at $5 \times 10^4$ cells/ml. Transfected J558L cells were then selected in the presence of medium containing xanthine (Sigma) and mycophenolic acid (Calbiochem, LaJolla, Calif.) (selective medium). The selective medium was applied 24 hr after transfection and positive clones (i.e., clones which grew in the selective medium) were screened two weeks later. Clones that secreted the fusion protein were identified using an ELISA for human IgG1. A good secreting clone was identified and designated clone no. 15. Clone no. 15 cells were metabolically labelled with [$^{35}$S]methionine and the secreted proteins were immunoprecipitated with protein A and the precipitated proteins were resolved on an SDS polyacrylamide gel. The mCTLA4-Hγ1 protein was found to migrate on SDS-PAGE gels as a monomer of approximately 60,000 MW under reducing conditions and as a dimer under non-reducing conditions.

Purified preparations of mCTLA4-Hγ1 protein were obtained by affinity chromatography of culture supernatants of clone no. 15 cells on a protein A-Sepharose (Zymed, South San Francisco, Calif.) column. Briefly, J558 cells expressing the mCTLA4-Hγ1 protein were grown in IMDM supplemented with 5% FCS, glutamine, 2ME and antibiotics. Culture supernatants were collected from the cells and centrifuged at 1500×g to remove any remaining cells and the clarified supernatant was filtered through a 0.4 micron pore size. The filtered supernatant was adjusted to pH 8.5 using IN NaOH; the supernatant was then passed over a 2 ml (packed volume) protein A-Sepharose column at a flow rate of 2 ml/min. It is noted that the J558 cell line produces an additional immunoglobulin (i.e., besides the mouse CTLAIg fusion protein) that binds to protein G; therefore the use of protein G resins is not recommended for the purification of the mCTLA4-Hγ1 protein from transfected J558 cells.

The protein A column was washed with 20 to 30 column volumes of PBS and the fusion protein was eluted with 50 mM diethylamine (pH 11.0). Two milliliter fractions were collected into tubes containing 0.2 ml 1M Tris-HC1 to neutralize the pH of the sample. The absorbance at 280 nm was determined and used to assess the protein concentration of each fraction. Fractions containing protein were combined and dialyzed overnight against 2 to 3 changes of PBS (1 liter per change). The presence of mCTLA4-Hγ1 protein was confirmed by SDS-PAGE, which showed a band of approximately 40 kD (the predicted molecular weight of the fusion protein). In addition, the purified mCTLA4-Hγ1 protein was tested in an ELISA using an antihuman IgG1 antibody (HP6058; the HP6058 hybridoma (ATCC CRL 1786) was used as the source of HP6058 antibodies).

b) Immunization of Hamsters

To immunize hamsters with the mouse CTLA-4 fusion protein, purified mCTLA4-Hγl protein (hereafter referred to as CTLA-4 lg) was used to coat heat-killed *Staphylococcus aureus* (StaphA) bacteria cells (Calbiochem, LaJolla, Calif.). Six week old Golden Syrian hamsters (Harlan Sprague Dawley, Indianapolis, In.) were injected in the footpad with 50 μl (packed volume) of heat-killed StaphA bacteria coated with approximately 100 μg of CTLA-41 g suspended in 0.2 ml of PBS. The StaphA cells were coated as follows.

StaphA cells were prepared according to the manufacturer's protocol to a concentration of 10% w/v in saline (0.9% NaCl). One ml of the bacterial cell slurry was centrifuged at 1,400×g to pellet the bacteria and the supernatant was removed. A 1 ml solution containing approximately 100 μg of purified CTLA-41 lg in PBS was added to the pellet and the mixture was incubated at 37° C. for 2 hours with agitation. The bacteria were then pelleted by centrifugation as described above; the pellet was washed twice with 1 ml of PBS/wash. The CTLA-41lg-coated bacterial cells were then resuspended in approximately 200 μl of PBS; 50 μl of this preparation was injected per footpad.

A total of five injections were given per hamster. On the day of the final boost and prior to the injection, approximately 100 μl of serum was obtained by intraocular bleeding performed by the Office of Laboratory Animal Care staff (Univ. of Calif, Berkeley). This serum was analyzed in comparison to serum obtained by the identical methodology prior to the first injection.

A CTLA-41 lg binding ELISA was utilized to demonstrate the presence of antibody that recognized the CTLA-41g fusion protein in the post-immunization bleed. The CTLA-41 lg binding ELISA was conducted as follows. CTLA-41 lg fusion protein or CD41 lg fusion protein was used to coat the wells of 96 well modified flatbottom ELISA plates (Corning, Corning, N.Y.).

CD41 lg is a fusion protein that consists of the extracellular domain of mouse CD4 and the hinge, CH2 and CH3 domains of human IgGI [Traunecker et al., supra.]; the CD41 lg protein was used as a negative control in the ELISA assays. The CD41 lg fusion protein was prepared from transfected J558 cells and purified by affinity chromatography on protein A Sepharose as described for the mCTLA4-Hμl (i.e., the CTLA-41 lg) fusion protein in section (a) above.

Fifty microliters of the fusion proteins, at a concentration of 1 μg/ml in 0.4% gelatin in PBS were placed in the wells. The plates were incubated at 37° C. for 2–3 hours to allow the proteins to absorb; the plates were then washed three times using 150 μl of 0.9% NaCl containing 0.05% Tween-20. The remaining protein binding sites in the wells were then blocked using 0.4% gelatin in PBS (blocking buffer) for 30 min at 37° C; following the blocking step, the plates were washed twice with 0.9% NaCI containing 0.05% Tween-20. Fifty microliters of solution containing antiCTLA-4 antibodies (i.e., serum from immunized hamsters, purified antibodies or culture supernatants) were added into triplicate wells and the plates were incubated for 2–3 hours at 37° C. To assess the amount of anti-CTLA-4 antibodies present in the serum of immunized hamsters, the initial post-immunization bleeds were tested using dilutions ranging from 1:1000 to 1:100 (diluted into PBS containing 0.4% gelatin).

The wells were then washed three times using 150 gl of 0.9% NaCl containing 0.05% Tween-20. Fifty microliters of a solution containing goat anti-hamster IgG polyclonal sera conjugated to horseradish peroxidase (CalTag, South San Francisco, Calif.) at a concentration of 1 μg/ml in blocking buffer was added to the wells and the plates were incubated for 1 hour at 37° C. The plates were then washed four times with 0.9% NaCl containing 0.05% Tween-20. A solution containing 0.55 mg/ml ABTS 2,2'-Azino-bis (3-ethylbenzthiazoline-6-sulfonic acid) in citrate buffer [0.1M citric acid (pH 4.35)] was added and the plates were incubated for approximately 20 min at 37° C. The plates were then read at 405 nm using a BioTech plate reader (Beckman Instruments, Palo Alto, Calif.) to assess the absorbance of the green reaction product.

The results of the CTLA-41 lg binding ELISA demonstrated the presence of antibody that recognized the CTLA-41g fusion protein in the post-immunization bleed at serum dilutions 1000-fold greater than the dilution at which background could be detected using the pre-immune bleed.

C) Isolation of Hybridoma Lines Secreting Anti-mouse CTLA-4 Antibodies

Three days following the final injection, draining lymph nodes were removed from the hamsters. Lymphocytes were isolated from the popliteal lymph nodes which drain the hind-limbs. Cell suspensions were made from the isolated lymph nodes as follows. The dissected nodes were placed in a tissue culture dish (Falcon Plastics, Mountain View, Calif.) containing RPMI medium (GibcoBRL, Gaithersburg, Md.) supplemented with 10% FCS (BioWhittaker, Walkersville, Md.). Lymphocytes were released from the nodes by gentle grinding of the nodes with frosted glass slides; the lymphocyte suspensions were counted using a hemocytometer.

The lymphocytes isolated from the immunized hamsters were fused to the fusion cell partner, P3X3.Ag8.653 (ATCC CRL 1580). P3X3.Ag8.653 cells were split 1:20 every 3 days prior to the fusion in IMDM (Univ. of Calif., San Francisco Tissue Culture Facility) containing 20% FCS (fetal calf serum) (BioWhittaker, Walkersville, Md.), 50 μdM 2-ME, 50 μM gentamicin.

The fusion with the myeloma line used a standard polyethylene glycol fusion technique [McKearn et al., Immunol. Rev. 47:91 (1979)]. Briefly, sterile lymphocyte cell suspensions were prepared in serum free Iscove's Modified Dulbecco's Media (IMDM). The lymphocytes were washed twice with IMDM and adjusted to a density of $12.5 \times 10^6$ cells/ml.

P3X3.Ag8.653 cells (grown as described above) were washed twice with serum free IMDM [these cells were centrifuged for 5 minutes at 1000 r.p.m. in a TJ-6 centrifuge (Beckman Instruments, Palo Alto, Calif.) at 25° C. to pellet the cells] and the P3X3.Ag8.653 cell density was adjusted to $5 \times 10^6$ cells/ml.

Four milliliters of the lymphocyte cell suspension were mixed with 1 ml of the washed P3X3.Ag8.653 cells in 60 mm tissue culture dish (Falcon). The tissue culture dishes were placed in microtiter plate carriers (Beckman Instruments, Palo Alto, Calif.) and centrifuged at 250×g (1200 r.p.m.; TJ-6 centrifuge) for 5 minutes to generate an adherent monolayer of cells on the bottom of the dish. The supernatant was aspirated from the dishes and the dishes were neatly flooded with 1 ml of 50% polyethylene glycol (PEG 1500, Boehringer Mannheim) in IMDM; the PEG solution was prepared by warming 4 ml of PEG 1500 and 4 ml of IMDM separately in 60° C. water bath and then combining by aspiration of the PEG into a pipette followed by the IMDM and mixing thoroughly. After 30 seconds at room temperature, the dishes were flooded with 5 ml of serum free IMDM.

Following the final wash on the day of the fusion, the cells were left in the 60 mm dish with 5 ml of IMDM medium containing FCS for 12 hours at 37° C with 5% $CO_2$. On the following day, the fused cells were diluted into 100 ml of IMDM containing 20% FCS and 1 HAT media (Boehringer Mannheim, N.J.) and 100 μl was plated per well in 96 well flat bottom plates. After 5 and 9 days, an additional 50 μl of media was added to each well. Thereafter, 50 μl of media was removed and fresh media added at 3 day intervals. Once cell numbers were within the 1000–5000 per well range, hybridoma supernatants were tested for reactivity to CTLA-4 lg and for a lack of reactivity to CD4lg by ELISA as described in section (b) above. Hybridoma supernatants were used undiluted in the ELISA (50 μl/well).

Hybridomas from positive wells were repetitively cloned by limiting dilution in the presence of irradiated mouse thymocyte feeder layers. A hybridoma line secreting a monoclonal antibody, termed antibody 9H10, was selected by the following criteria: 1) reactivity against CTLA-4lg but not CD4lg in ELISAs; 2) the ability to block CTLA-41 lg binding to B7 transfectants; 3) the ability to stain activated T cells but not freshly isolated T cells; and 4) the ability to stain a CTLA-4 transfectant but not control transfectants.

The ability of antibody 9H10 to block CTLA41 lg binding to B7 transfectants was demonstrated as follows. Approximately 10 μl of mAb 9H10 was incubated at 22° C. for 30 min with 1 μg of CTLA-41 lg fusion protein in a final volume of 50 μl of a solution comprising PBS. To this mixture was added $2 \times 10^5$ B7-EL-4 cells, suspended in 10 μl ice-cold PBS containing 1% calf serum and 0.05% sodium azide. B7-EL-4 cells are the C57BL/6-derived EL4 thymoma cell line transfected with an expression vector encoding the mouse B7 cell surface protein, as described in Townsend et al. *Cancer Res.* 54:6477–83 (1994).

The resulting mixture was then incubated on ice for 30 minutes, followed by two washes with 4 ml/wash of PBS containing 1% calf serum and 0.05% sodium azide. The cells were then stained with fluorescein isothiocynate (FITC)-conjugated anti-human IgG (Caltag, South San Francisco, Calif.). As a negative control for this experiment, the CTLA-41 lg fusion protein was incubated with either a control hamster lgG or the EL-4 parent cell line. The cells were analyzed on a FACScan (BectonDickinson, Mountain View, Calif.); the LYSIS II program (Becton Dickinson) was used to electronically gate on relevant populations. In most experiments, 10,000 live gated events were collected for analysis. The results showed that the 9H10 antibody blocked CTLA-4 binding to B7-EL-4 cells.

The ability of the 9H10 antibody to stain activated T cells but not freshly isolated T cells was demonstrated as follows. Fresh and activated splenocytes were generated. Spleens from 4–6 week BALB/c mice were harvested and minced, and suspensions were treated with hemolytic Gey's solution to remove the red blood cells, a standard technique in the art [Mishell and Shiigi, Selected Methods in Cellular Immunology, W. H. Freeman and Co., San Francisco (1980) pp.23–24]. The cells were cultured in RPMI containing 10% fetal calf serum, with soluble anti-CD-3 antibody at 10 μg/ml added to activate one portion of the cell population. The other portion of the splenocytes was not treated with anti-CD3 and represents fresh (but not activated splenocytes). The two cell populations were then stained with either 1) a combination of FITC-conjugated 9H10 (the anti-CTLA-4 antibody; 5 μg of antibody) and PE-conjugated Thy1.2 or 2) a combination of FITC-conjugated hamster lg and PE-conjugated Thy1.2. The data were analyzed on a FACScan and was electronically gated for Thy1.2 positive cells to analyze only the relevant T cell population. The results of this experiment demonstrated that the 9H10 antibody stained activated (i.e., CTLA-4 expressing) but not freshly isolated T cells.

The ability of the 9H10 antibody to stain a CTLA-4 transfectant but not control transfectants was demonstrated as follows. A parent CHO (Chinese Hamster Ovary, CHO-K1 cells) cell line (ATCC CCL 61) was transfected with pSRlneo.CTLA-4. pSRlneo.CTLA-4 contains the entire 1.9 kb cDNA encoding the mouse CTLA-4 protein [Brunet et al., *Nature* 328:267 (1987)] inserted into the pSRlneo expression vector. Cells transfected with the pSRlneo.CTLA vector express the mouse CTLA-4 protein on the cell surface.

The parent (i.e., CHO-K1 cells) and transfected cells were stained either 1) a combination of FITC-conjugated 9H10 (the anti-CTLA-4 antibody; 5 μg of antibody) and PE-conjugated Thy1.2 or 2) a combination of FITC-conjugated hamster lg and PE-conjugated Thy1.2. The data was electronically gated for Thy1.2 positive cells to analyze only the relevant T cell population. The results of this experiment demonstrated that the 9H10 antibody stains CTLA-4 transfectants but not control transfectants.

The above results demonstrated that the 9H10 monoclonal antibody reacts specifically with the mouse CTLA-4 protein.

EXAMPLE 2

Anti-CTLA-4 Monoclonal Antibodies Cause Rejection of V51BLim10 Tumors in Mice

The anti-mouse CTLA-4 monoclonal antibody, 9H10, was used to treat mice that received injections of a colon carcinoma cell line. The injection of the 9H10 mAb along with V51BLim10 tumor cells resulted in the complete rejection of the tumor cells in the experimental animals. In contrast, mice injected with an anti-CD28 mAb and V51BLim10 cells or mice injected with V51BLim10 cells alone both developed tumors which exhibited a steady increase in average tumor size over a period of four weeks.

a) Generation of the V51BLim10 Cell Line

The V51BLim10 cell line was generated by transfection of the SRlneo expression vector into the 51BLim10 cell line. The 51BLim cell line is a colon carcinoma cell line that provides an accurate animal model for colon cancer metastasis in humans. Bresalier, et al., *Cancer Res.* 47:1398 (1987).

The V51BLim10 cell line used in the present experiments was generated as follows. The murine colon cancer cell line 51B established by Corbett et al., *Cancer Res.* 35:2434–9 (1975) was injected into the cecal wall of BALB/c mice; the resulting colonic tumors were found to spontaneously metastasize to the liver in a minority of the injected mice. Bresalier et al., *Cancer Res.* 47:1398 (1987). Tumor cell lines having progressively increased metastatic activity were developed by collecting cells from the original metastases, which were then used for successive reinjection into the ceca of additional mice. These cell lines were termed 51BLim-1 through 51BLim-5 where the number following the dash refers to the number of metastatic cycles.

A 51 B metastatic derivative obtained from Dr. Warren at the University of California San Francisco was designated 51BLim10; the 51BLim10 cell line corresponds to the 51BLiM5 cell line described by Bresalier, et al., Cancer Res. 47:1398 (1987).

The SRIneo expression vector was transfected into the 51 BLiM-10 cell line to generate the V51BLim10 cell as described [Townsend et al. Cancer Res. 54:6477–83 (1994)]. The SR1neo expression vector (obtained from L. Lanier at DNAX Research Institute of Molecular and Cellular Biology, Palo Alto, Calif.) allows the expression of a gene of interest under the transcriptional control of the HTLV-1 LTR. The SRIneo vector also contains the neo gene under the transcriptional control of the SV40 promoter/enhancer. The presence of the neo gene allows for the selection of transfected cells containing the SRIneo vector.

The SRIneo expression vector was transfected into 51 BLiM-10 cells by electroporation using a BTX T 800 electroporator (BTX, Inc., San Diego, Calif.). Five pulses for 99 μs each at 450 or 600 V were applied. The electroporation was carried out in a final reaction volume of 750 μl of a solution comprising 270 mM sucrose, 7mM $NaPO_4$ (pH 7.4), 1 mM $MgCl_2$, $5\times10^6$ 51B LiM-10 cells and 50 μg of the SRIneo expression vector. Following electroporation, the cells were cultured for 24 hours in complete medium [Eagle's MEM (Univ. of Calif. at San Francisco Cell Culture Facility, San Francisco, Calif.) supplemented with 10% FCS (Sigma), nonessential amino acids, MEM vitamin solution, L-glutamine, sodium pyruvate, gentamicin (all from Irvine Scientific, Santa Ana, Calif.) and 7.5% sodium bicarbonate (Sigma)] at 37° C. Selection medium [complete medium containing 1 mg/ml Geneticin (G418 sulfate, GIBCO, Grand Island, N.Y.)]. After 14 days of culture in the selection medium, drug resistant cells were pooled and used in subsequent experiments as a polyclonal population referred to as V51BLim10.

V51BLim10 tumor cells were maintained in Eagle's MEM (Univ. of Calif. at San Francisco Cell Culture Facility, San Francisco, Calif.) supplemented with 10% FCS (Sigma), non-essential amino acids, MEM vitamin solution, L-glutamine, sodium pyruvate, gentarnicin, penicillin-streptomycin (all from Irvine Scientific, Santa Ana, Calif.) and 1 mg/ml Geneticin. Cell cultures were established from low passage (i.e, less than 10 passages) frozen aliquots and maintained in culture for no more than 30 days prior to use.

V51BLim10 cells and the parental 51BLim10 cells were found to exhibit similar in vitro and in vivo growth rates. The expression of the neomycin resistance gene in the V51BLim10 cells and a variety of other tumor cell lines has had no effect on the tumorigenicity or growth rate of tumors from the injected cells.

b) Injection of Mice with V51BLim10 Tumor Cells and Monoclonal Antibodies.

The V5IBLim10 tumor cells were harvested from tissue culture plates with trypsin-EDTA (Sigma), washed three times in serum-free media (Eagle's MEM) and suspended at a concentration of $2\times10^7$ cells/ml.

The mice used in this experiment were 6–8 week old female BALB/c mice (Charles River Laboratories, Wilmington, Mass.). Groups of five mice were anesthetized by methoxyflurane inhalation, ear notched for identification, and injected with 200 μl of the V51BLim10 tumor cell suspension ($4\times10^6$) subcutaneously in the left flank. Treated groups received 100 μg intraperitoneal injections of the antiCTLA-4 mAb 9H10 described above, or alternatively the anti-CD28 mAb, 37.51, on the same day, and additional 50 μg i.p. injections on days 3 and 6 following the injection of the tumor cells (designated by the darkened arrows in FIG. 1). The monoclonal anti-CD28, 37.51, is directed against the mouse CD28 protein [Gross et al., *J. Immunol.* 149:380 (1992)] and served as a negative control.

The mice were monitored for subcutaneous tumor growth and the bisecting diameters of developing tumors were measured with calipers. All of the mice left untreated, or treated with anti-CD28 antibody, developed progressively growing tumors and required euthanasia by 35 days after inoculation. In contrast, all mice treated with anti-CTLA-4 antibody completely rejected their tumors after a short period of limited growth. As shown in FIG. 1A, the average tumor area in mm2 (displayed along the y axis) decreased gradually starting at approximately day 14 post-tumor injection (displayed along the x axis), decreasing to zero at approximately day 24. Anti-CTLA-4 treatment was less effective at smaller tumor doses. FIG. 1B shows the average tumor size in mice injected with $2\times10^6$ tumor cells and treated as described above with anti-CTLA-4 antibody or an irrelevent hamster antibody. Anti-CTLA-4 antibody treatment continued to have a dramatic effect on tumor growth, but one mouse developed a tumor quickly, and another much later. FIG. 1C illustrates the individual tumor growth in mice injected with $2\times10^6$ V51BLim10 cells. Three of the mice remained tumor free beyond 80 days. It is clear that CTLA-4 blockade significantly enhanced rejection of the B7 negative tumor cells.

c) Injection of Mice with B7-51BLim10 Tumor Cells and Monoclonal Antibodies.

51BLim10 cells were transfected as described above, with a plasmid containing the gene for murine B7-1, and cloned by limiting dilution. The B7-51BLim10 tumor cells were harvested from tissue culture plates with trypsin-EDTA (Sigma), washed three times in serum-free media (Eagle's MEM) and suspended at a concentration of $2\times10^7$ cells/ml.

The mice used in this experiment were 6–8 week old female BALB/c mice (Charles River Laboratories, Wilmington, Mass.). Groups of five mice were anesthetized by methoxyflurane inhalation, ear notched for identification, and injected with 100 μl of the B7-51BLim10 tumor cell suspension ($4\times10^6$) subcutaneously in the left flank. Treated groups received 100 μg intraperitoneal injections of the antiCTLA-4 mAb 9H10 described above, or alternatively the anti-CD28 mAb, 37.51. Injections of 100, 50 and 50 μg were given on days 0.3 and 6, respectively (injection days are designated by the darkened arrows in FIG. 2). The monoclonal anti-CD28, 37.51, is directed against the mouse CD28 protein [Gross et al., J. Immunol. 149:380 (1992)] and served as a negative control.

The mice were monitored for subcutaneous tumor growth and the bisecting diameters of developing tumors were measured with calipers. The data from this experiment is shown in FIG. 2. Treatment with anti-CTLA-4 antibodies inhibited B7-51BLim10 tumor growth as compared to the anti-CD28 and control groups all mice in the untreated and anti-CD28 treated groups developed small tumors that grew progressively for five to ten days and then ultimately regressed in eight of the ten mice by about day 23 post injection. The two small tumors that did not regress remained static for over 90 days. In contrast, 3 of the 5 mice treated with anti-CTLA-4 antibody developed very small tumors, and all of these regressed completely by day 17.

d) Anti-CTLA-4 induced rejection of V51BLim10 tumor cells results in protection against subsequent challenge with wild-type colon carcinoma cells.

Five anti-CTLA-4 treated mice that had completely rejected V51BLim10 tumor cells were rechallenged 70 days later with $4\times10^6$ wild-type 51BLim1O tumor cells injected sub-cutaneously in the opposite flank. Five naive mice were also injected as controls. Tumor diameters were measured and reported as described. Prior tumor rejection resulted in significant protection against secondary challenge as compared to naive controls. All control mice developed progressively growing tumors, developed massive tumor burdens, and were euthanized on day 35 post-inoculation. 3 of 5 previously immunized mice remained tumor free 70 days after challenge. Only one of the previously immunized mice had a detectable tumor by day 14, and growth of this tumor was very slow. Utimately, two more tumors developed in the immunized mice 42 days after challenge. The data is shown in FIG. 3. These results demonstrated that tumor rejection mediated by CTLA-4 blockade resulted in immunologic memory.

e) Anti-CTLA-4 treatment reduces the growth of established tumors.

Groups of mice were injected s.c. with $2 \times 10^6$ $^{51}$BLim10 tumor cells. Control animals (n=10) were injected i.p. with 100 μg irrelevant hamster antibody on days 0, 3, 6 and 9, as indicated by the upward pointing arrows in FIG. 4. One anti-CTLA-4 treatment group received i.p. injections on the same days. The other treated mice (n=5) were given i.p. injections of anti-CTLA-4 antibody beginning on day 7 and subsequently on days 10, 13 and 16 (downward pointing arrows). Data is shown in FIG. 4. Mice treated with anti-CTLA-4 antibodies at either time point had significantly reduced tumor growth compared to untreated controls. Delaying treatment appeared to be more effective, with 2 of 5 mice remaining tumor free beyond thirty days after inoculation.

f) Anti-CTLA-4 treatment reduces the growth of the murine fibrosarcoma SA1N.

The effects of anti-CTLA-4 treatment were not limited to carcinoma cell lines. Similar results were obtained with a rapidly growing fibrosarcoma cell line of A/JCr mice. Groups of mice were injected s.c. in the flank with a suspension of $1 \times 10^6$ SA1N fibrosarcoma cells. Treated groups were injected i.p. with 100 μg anti-CTLA-4 or irrelevant hamster control antibody at days 0, 3 and 6, as indicated by the arrows in FIG. 5. All control animals were killed by day 30. Two of five anti-CTLA-4 treated animals remained tumor free at day 55. Data is shown in FIG. 5.

EXAMPLE 3

Anti-CTLA-4 Monoclonal Antibodies Act as an Adjuvant a) Preparation of immunogen DNP-KLH was obtained from Calbiochem (San Diego, Calif.) and was suspended in deionized water at 1 mg/ml, 100 ng/ml or 10 pg/ml. One ml of Freund's Complete Adjuvant (Difco, Mich.) was added to each 1 ml of the DNP-KLH preparations. These were then emulsified in two 5 ml syringes connected by a double-ended luer lock connector by rapid passage through the luer lock, as described in Current Protocols in Immunoloay, Colligan et al., eds., section 2.4.

30 minutes prior to injection of the immunogen, C57Bl/6 mice of 4–6 weeks in age were injected in the peritoneum using a 23 gauge syringe with 200 μg of non-specific control hamster antibody or with 200 μg of anti-CTLA-4 antibody 9H10 (both in 200 μl total volume). The mice were subsequently injected subcutaneously using a 21 gauge syringe at two sites on the back, with 200 μ of the immunogen in the form described above, giving a dose of 100 μg, 10 ng or 1 pg/mouse, respectively. After three days the antibody injections were repeated.

Ten days following the first treatment, the animals were euthanized. Blood was obtained by heart puncture and removed to eppendorf tubes. These samples were allowed to coagulate at 4° C. overnight, and were then centrifuged to obtain sera.

Sera was analyzed for isotype specific antibodies recognizing DNP using a standard isotype ELISA, as described in Current Protocols in Immunology (supra.) section 2.1. Briefly, DNP was plated at 100 ng/ml in 50 gl volume in each well of a 96 well Corning modified round-bottom ELISA plate. The wells are blocked using buffers as described. Three-fold serial dilutions of each sera, starting at 1:100 are added to each well. These are incubated for one hour at 25° C., and washed with wash buffer. Isotypes are detected by using mouse specific antibodies as detecting agents at 1 μg/ml in 50 μl of blocking buffer incubated for one hour. The isotype antibodies are biotinylated, and detection is achieved by incubating with avidin-horseradish peroxidase, washing and addition of peroxidase substrate (ABTS, Sigma, Mo.). Stop buffer is added, and the absorbance of each well read with an ELISA reader at a wave length of 490–498 nm within 5–8 min of stopping the reaction.

The results are shown in FIGS. 6A to 6E. Each of the panels illustrates the concentration of a different isotype in the serum sample. The y axis shows the O.D. reading, where an increase in O.D. indicates increased concentration of antibodies in the serum having that isotype. The x axis shows the amount of antigen that was injected, 100 μg, 10 ng or 1 pg per animal, respectively. It can be seen that anti-CTLA-4 antibody increases class switching to IgG1, IgG2$a$ and IgG2$b$ at the higher dose of antigen.

Analysis of T cell function was performed as follows. Lymph node cells were isolated and stimulated in vitro for 72 hours with KLH. The axillary, inguinal, mesenteric, brachial, cervical and popliteal lymph nodes were removed to a dish containing RPMI-complete (10% FCS (Hyclone, Montana), 2 mM glutamine, 50 μM β-mercaptoethanol, 50 μg/ml gentamycin). The lymph nodes were minced to obtain single cell suspensions, filtered through a nytex mesh to remove particulate, and counted using a hemocytometer. Cells were plated in 150 ul of RPMI-complete in 96 well round bottom cluster plates at either $5 \times 10^5$, $2.5 \times 10^5$, or $1.25 \times 10^5$ cells/well. KLH solutions in RPMI-complete were added to final concentrations of 100, 10, 1 or 0 μg/ml and the plates were incubated at 37° C. for 64 hours in humidified incubators with 5% $CO_2$. After 64 hours, 20 μl of RPMI-complete containing 1 μCi of $^3$H-thymidine was added to each well, and the plates were incubated an additional eight hours. At this time, cultures were harvested onto glass fiber filters using an Inotech 96 well harvester. Filters were dried and counted using a Packard Matrix counter. Each condition was performed in triplicate, and data represents the mean of triplicate values.

The results are shown in FIGS. 7A to 7B. The top row shows a constant number of cells ($5 \times 10^5$ cells), with varying concentrations of antigen (shown on the x axis). The y axis shows incorporation of $^3$H-thymidine, a measure of cell proliferation. The lower panel shows a constant antigen concentration (10 μg/ml), with varying numbers of cells (shown on the x axis). The data indicates that CTLA-4 blockade strongly upregulates the T cell response to the higher doses of antigen.

EXAMPLE 4

Generation of Antibodies Directed Acainst Human CTLA-4 Proteins

Anti-human CTLA-4 antibodies are generated as follows.

a) Human CTLA-4 Proteins for Immunization of Host Animals

Immunogens comprising human CTLA-4 proteins contain all or a portion of the extracellular domain of the human CTLA-4 protein. The extracellular domain of the human CTLA-4 protein comprises amino acid residues 38-161, as listed in the database references.

The human CTLA-4 immunogen comprises the entire human CTLA-4 protein or a fusion protein comprising the extracellular domain of human CTLA-4 and a fusion partner. The immunogen comprises the entire human CTLA-4 protein inserted into the membrane of a cell; the cell expressing human CTLA-4 on the surface is used to immunize a host animal.

Immunogens comprising portions of the human CTLA-4 protein are generated using the PCR to amplify DNA sequences encoding the human CTLA-4 protein from mRNA from H38 cells, an HTLV II-associated leukemia line (R. Gallo, National Cancer Institute). The mRNA is reverse transcribed to generate first strand cDNA. The cDNA is then amplified. These sequences are linked to sequences that encode a fusion partner, as described in Linsley et al. [*J. Exp. Med.* 174:561 (19991)]. The expression vector encodes a fusion protein termed CTLA41 lg, which comprises (from amino- to carboxy-termini) the signal peptide from oncostatin M, the extracellular domain of human CTLA-4 and the H, CH2 and CH3 domains of human IgG1. The signal peptide from oncostatin M is used in place of the naturally occurring human CTLA-4 signal peptide. The cysteine residues found in the wild-type hinge domain of the human IgG1 molecule were mutated to serines in the construction of the vector encoding the CTLA41 g protein (Linsley et al., supra).

b) Immunization of Host Animals With Human CTLA-4 Proteins

To immunize animals with immunogens comprising human CTLA-4 proteins, non-human host animals are employed. The immunogen comprising a human CTLA-4 lg fusion protein (e.g., CTLA41 g), is used to coat heat-killed Staphylococcus A (StaphA) bacteria cells as described in Example 1b. Six week old BALB/c mice are injected in the footpad with 50 μl (packed volume) of heat-killed StaphA bacteria coated with approximately 100 μg of CTLA-41 lg suspended in 0.2 ml of PBS.

A total of five injections are given per mouse. On the day of the final boost and prior to the injection, approximately 100 μl of serum is obtained by intraocular bleeding as described in Example 1b. The serum is analyzed in companion to serum obtained by the identical methodology prior to the first injection (i.e., pre-immune serum).

A human CTLA-41 g binding ELISA is utilized to demonstrate the presence of antibody that recognizes the human CTLA-41 g fusion protein in the post-immunization bleed. The human CTLA-41 g binding ELISA is conducted as described above in Example 1b with the exception that the ELISA plates are coated with human CTLA-4 protein.

The serum and lymph nodes of the immunized mice containing antibody that recognizes the human CTLA-41 g fusion protein in the post-immunization bleed at serum dilutions 1000-fold greater than the dilution at which background could be detected are collected. Lymphocytes are prepared from draining lymph nodes in the immunized mice and are then used for the generation of monoclonal antibodies directed against the human CTLA-4 protein as described above in Example 1c.

Immunogens comprising transformed cells expressing the human CTLA-4 protein on the cell surface are prepared as follows. Expression vectors encoding the entire human CTLA-4 protein are used to transfect the mouse lymphoma cell line EL4 (ATCC TIB 39). Transfected EL4 cells are injected into mice using $1\times10^6$ to $1\times10^7$ transfected cells/injection. The transfected cells are injected in a solution comprising PBS. The mice may be injected either i.p. or in the hind footpad. When i.p. injections are given, a total of approximately 4 injections are administered. When the footpad is used as the site of injection, a total of approximately 5 injections are administered. Serum is collected from the immunized animals and tested for the presence of antibodies directed against the human CTLA-4 protein using an ELISA as described in Example 1b, with the exception that the plates are coated with human CTLA-4 proteins.

c) Isolation of Hybridoma Lines Secreting Anti-Human CTLA-4 Antibodies

Lymphocytes are isolated from draining lymph nodes or the spleens of animals immunized with the human CTLA-4 immunogen and fused to P3X3.Ag8.653 cells to generate hybridoma cell lines using the PEG fusion protocol described in Example 1c. Culture supernatant from wells containing 1000–5000 cells/well are tested for reactivity to human CTLA-4 and for lack of reactivity to a non-CTLA-4 protein such as human CD4 using an ELISA assay.

Hybridomas from positive wells are repetitively cloned by limiting dilution as described in Example 1c. Hybridoma lines secreting monoclonal antibodies that are reactive against human CTLA-4 proteins but not irrelevant human proteins (e.g., human CD4), and that have the ability to stain cells human CTLA-4 transfectants but not control transfectants are selected for production of anti-human CTLA-4 monoclonal antibodies.

EXAMPLE 5

Ex Vivo Stimulation of Tumor Infiltratina Lvmphocytes (TiLs)

Host cells are stimulated ex vivo, allowing them to differentiate into tumor-specific immune effector cells. The cells are then reintroduced into the same host to mediate anticancer therapeutic effects.

a) Isolation of Tumor-Infiltrating Lymphocytes (TILs)

Tumor-infiltrating lymphocytes are obtained using standard techniques. Solid tumors (freshly resected or cryopreserved) are dispersed into single cell suspensions by overnight enzymatic digestion [e.g., stirring overnight at room temperature in RPMI 1640 medium containing 0.01% hyaluronidase type V, 0.002% DNAse type 1, 0.1% collagenase type IV (Sigma, St. Louis), and antibiotics]. Tumor suspensions are then passed over Ficoll-Hypaque gradients (Lymphocyte Separation Medium, Organon Teknika Corp., Durham, N.C.). The gradient interfaces contain viable tumor cells and mononuclear cells are washed, adjusted to a total cell concentration of 2.5 to 5.0×10⁵ cells/ml and cultured in complete medium. Complete medium comprises RPMI 1640 with 10% heat-inactivated type-compatible human serum, penicillin 50 lU/ml and streptomycin 50 μg/ml (Biofluids, Rockville, Md.), gentamicin 50 μg/ml (GIBCO Laboratories, Chagrin Falls, Ohio), amphotericin 250 ng/ml (Funglzone, Squibb, Flow Laboratories, McLean, Va.), HEPES buffer 10 mM (Biofluids), and L-glutamine 2 mM (MA Bioproducts, Walkersville, Md.). Conditioned medium from 3- to 4-day autologous or allogeneic lymphokine-activated killer (LAK) cell cultures (see below) is added at a final concentration of 20% (v/v). Recombinant IL-2 is added at a final concentration of 1000 U/ml.

Cultures are maintained at 37° C. in a 5% $CO_2$-humidified atmosphere. Cultures are fed weekly by harvesting, pelletting and resuspending cells at 2.5×10⁶ cells/ml in fresh medium. Over an initial period (e.g., 2 to 3 weeks) of culture, the lymphocytes selectively proliferate, while the remaining tumor cells typically disappear completely.

To make LAK cell cultures, peripheral blood lymphocytes (PBL) are obtained from patients or normal donors. After passage over Ficoll-Hypaque gradients, cells are cultured at a concentration of 1×10⁶/ml in RPMI 1640 medium with 2% human serum, antibiotics, glutamme, and HEPES buffer. Recombinant IL-2 is added at 1000 U/ml. Cultures are maintained for 3 to 7 days in a humidified 5% $CO_2$ atmosphere at 37°.

b) Ex Vivo Stimulation of TILs

4×10⁶ cells, in 2 ml of culture medium containing the anti-CTLA-4 mAbs, are incubated in a well of 24-well plates at 37° C. in a 5% $CO_2$ atmosphere for 2 days. The culture medium comprises RPMI 1640 medium supplemented with 10% heat inactivated fetal calf serum, 0.1 mM nonessential amino acids, 1 μM sodium pyruvate, 2 mM freshly prepared L-glutamine, 100 μg/ml streptomycin, 100 U/ml penicillin, 50 μlg/mlg gentamicin, 0.5 μg/ml fungizone (all from GIBCO, Grand Island, N.Y.) and 5×10⁻⁵ M 2-ME (Sigma). The cells are harvested and washed.

The initially stimulated cells are further cultured at 3×10⁵/well in 2 ml of culture media with recombinant human IL-2 (available from Chiron Corp., Emeryville, Calif.; specific activity of 6 to 8×10⁶ U/mg protein; units equivalent to 2–3 International U). After 3 days incubation in IL-2, the cells are collected, washed, counted to determine the degree of proliferation, and resuspended in media suitable for intravenous (i.v.) administration (e.g. physiological buffered saline solutions). Bacterial cultures are performed to determine the existence of bacterial contamination prior to reinfusion of the activated cells.

After the activated TILs have been resuspended in a media suitable for injection, IV access is obtained in the host and the cell suspension is infused. Optionally, the host is treated with agents to promote the in vivo function and survival of the stimulated cells (e.g. IL-2).

The above results demonstrate that the subject treatment with CTLA-4 blocking agents increases the response of T cells to antigenic stimulation. The growth of tumor cells in vivo is greatly diminished in the presence of the the subject blocking agents. The effects are observed against unmanipulated, wild-type tumors. CTLA-4 blocking agents not only represent a novel approach to tumor therapy, but, by removing potentially competing inhibitory signals, may be a particularly useful adjunct to other therapeutic approaches involving the co-stimulatory pathway. Class switching by immunoglobulin producing cells, a measure of T cell help, is greatly increased. The T cell response to immunization with peptide antigens is also greatly increased by the treatment with the subject agents.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of increasing the response of a mammalian T cell to antigenic stimulation, the method comprising:

combining a T cell with an effective dose of a CTLA-4 blocking agent, wherein said blocking agent is capable of specifically binding to the extacellular domain of CTLA-4 and inhibiting CTLA-4 signaling;

wherein said dose is effective to increase said response of said mammalian T cell to antigenic stimulus.

2. A method according to claim 1, wherein said CTLA-4 blocking agent is an oligopeptide.

3. A method according to claim 1, wherein said oligopeptide is an antibody or fragment thereof.

4. A method according to claim 1, wherein said antigenic stimulus is a pathogen antigen.

5. A method according to claim 1, wherein said antigenic stimulus is a tumor antigen.

6. A method according to claim 1, wherein said antigenic stimulus is a vaccine.

7. A method of increasing the in vivo response of a mammalian T cell to antigenic stimulation, the method comprising:

combining a T cell with an effective dose of a CTLA-4 blocking agent, wherein said blocking agent is capable of specifically binding to the extracellular domain of CTLA-4 and inhibiting CTLA-4 signaling;

wherein said dose is effective to increase said in vivo response of said mammalian T cell to antigenic stimulus.

8. A method according to claim 7, wherein said CTLA-4 blocking agent is an oligopeptide.

9. A method according to claim 7, wherein said oligopeptide is an antibody or fragment thereof.

10. A method according to claim 7, wherein said antigenic stimulus is a pathogen antigen.

11. A method according to claim 7, wherein said antigenic stimulus is a tumor antigen.

12. A method according to claim 7, wherein said antigenic stimulus is a vaccine.

\* \* \* \* \*

UNITED STATES PATENT AND TRADEMARK OFFICE
CERTIFICATE OF CORRECTION

PATENT NO. : 5,855,887  
DATED : January 5, 1999  
INVENTOR(S) : James P. Allison et al.

It is certified that error appears in the above-identified patent and that said Letters Patent is hereby corrected as shown below:

Column 1,  
Line 45, change "energy" to -- "anergy" --.

Column 2,  
Line 47, change "absense or presence" to -- presence or absence --.

Column 4,  
Line 45, change "10⁻M" to -- $10^{-8}M$ --.

Column 7,  
Line 14, change "90104036" to -- 90/04036 --.  
Line 18, change "92102190" to -- 92/02190 --.  
Line 36, change "IgGi" to -- IgG1 --.

Column 12,  
Line 26, change "ρβAPr-1-neo-" to -- ρHβAPr-1-neo- --.

Column 13,  
Line 31, change "CTLA-411g" to -- CTLA-4Ig --.  
Line 41, change "CTLA-41 lg" to -- CTLA-4Ig --.  
Line 44, change "CTLA-41 lg" to -- CTLA-4Ig --.  
Line 45, change "CTLA-41 lg" to -- CTLA-4Ig --; and change "CD41 lg" to -- CD4Ig --.  
Line 48, change "CD41 lg" to -- CD4Ig--.  
Line 51, change "CD41 lg" to -- CD4Ig --.  
Line 52, change "CD41 lg" to -- CD4Ig --.  
Line 55, change "CTLA-41 lg" to -- CTLA-4Ig --.

Column 14,  
Line 8, change "150 gl" to -- 150 μl --.  
Line 23, change "CTLA-41 lg" to -- CTLA-4Ig --.  
Line 46, change "μIM" to -- μM --.

Column 15,  
Line 14, change 1 HAT" to -- 1X HAT --.  
Line 21, change "CD41 lg" to -- CD4Ig --.  
Line 29, change "CTLA-41 lg" to -- CTLA-4Ig --.  
Line 33, change "CTLA-41 lg" to -- CTLA-4Ig --.  
Line 36, change "CTLA-41 lg" to -- CTLA-4Ig --.  
Line 50, change "41 lg" to -- 4Ig --.

UNITED STATES PATENT AND TRADEMARK OFFICE
CERTIFICATE OF CORRECTION

PATENT NO.   : 5,855,887
DATED        : January 5, 1999
INVENTOR(S)  : James P. Allison et al.

It is certified that error appears in the above-identified patent and that said Letters Patent is hereby corrected as shown below:

Column 18,
Line 53, after "groups" insert -- for --.
Line 66, change "51BLim1O" to -- 51BLim10 --.

Column 19,
Line 17, change "$^{51}$BLim10" to -- 51BLim10 --.

Column 20,
Line 8, change "50 gl" to -- 50 µl --.
Line 44, change "150 ul" to -- 150 µl --.

Column 21,
Line 30, change "CTLA41 lg" to -- CTLA4Ig --.
Line 45, change "CTLA-4 lg" to -- CTLA-4Ig --.
Line 46, change "CTLA41 g" to -- CTLA4Ig --.
Line 50, change "CTLA-41 lg" to -- CTLA-4Ig --.

Column 23,
Line 38, change "50 µlg/mlg" to -- 50 µlg/ml --.

Signed and Sealed this

Eighth Day of October, 2002

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:1:

TTACTCTACT CCCTGAGGAG CTCAGCACAT TTGCC 3 5

( 2 ) INFORMATION FOR SEQ ID NO:2:

( i ) SEQUENCE CHARACTERISTICS:
        ( A ) LENGTH: 35 base pairs
        ( B ) TYPE: nucleic acid -continued

```
    ( C ) STRANDEDNESS: single
    ( D ) TOPOLOGY: linear ( i i ) MOLECULE TYPE: other nucleic acid
    ( A ) DESCRIPTION: /desc = "Primer"

( x i ) SEQUENCE DESCRIPTION: SEQ ID NO:2:

TATACTTACC  AGAATCCGGG  CATGGTTCTG  GATCA                              3 5
```